US010071126B2

(12) United States Patent
Kumon et al.

(10) Patent No.: US 10,071,126 B2
(45) Date of Patent: Sep. 11, 2018

(54) CONDITIONALLY REPLICATING ADENOVIRUS TO EXPRESS REIC GENE

(71) Applicants: National University Corporation Okayama University, Okayama-shi, Okayama (JP); Momotaro-Gene Inc., Okayama-shi, Okayama (JP); Industry-University Cooperation Foundation Hanyang University, Seongdong-gu, Seoul (KR)

(72) Inventors: Hiromi Kumon, Okayama (JP); Yasutomo Nasu, Okayama (JP); Masami Watanabe, Okayama (JP); Chae Ok Yun, Seoul (KR)

(73) Assignees: National University Corporation Okayama University, Okayama (JP); Momotaro-Gene Inc., Okayama (JP); Industry-University Cooperation Foundation Hanyang University, Seoul (KR)

( * ) Notice: Subject to any disclaimer, the term of this patent is extended or adjusted under 35 U.S.C. 154(b) by 17 days.

(21) Appl. No.: 15/313,674

(22) PCT Filed: May 26, 2015

(86) PCT No.: PCT/JP2015/065004
§ 371 (c)(1),
(2) Date: Nov. 23, 2016

(87) PCT Pub. No.: WO2015/182574
PCT Pub. Date: Dec. 3, 2015

(65) Prior Publication Data
US 2017/0202892 A1    Jul. 20, 2017

(30) Foreign Application Priority Data
May 28, 2014  (JP) ................. 2014-110672

(51) Int. Cl.
*A61K 35/761*  (2015.01)
*C12N 7/00*  (2006.01)

(52) U.S. Cl.
CPC .............. *A61K 35/761* (2013.01); *C12N 7/00* (2013.01); *C12N 2710/10033* (2013.01)

(58) Field of Classification Search
None
See application file for complete search history.

(56) References Cited
U.S. PATENT DOCUMENTS

| 9,222,107 | B2 * | 12/2015 | Kumon | .............. | C07K 14/4702 |
| 9,644,013 | B2 * | 5/2017 | Kumon | .............. | C07K 14/4703 |
| 2003/0099616 | A1 * | 5/2003 | Irving | ................ | A61K 48/0058 424/93.2 |
| 2007/0059287 | A1 | 3/2007 | Yun et al. | | |
| 2008/0132449 | A1 | 6/2008 | Yun et al. | | |
| 2013/0267025 | A1 | 10/2013 | Kumon et al. | | |
| 2013/0323206 | A1 | 12/2013 | Yun et al. | | |
| 2014/0147917 | A1 | 5/2014 | Kumon et al. | | |

FOREIGN PATENT DOCUMENTS

| JP | 2008-531010 A | 8/2008 |
| JP | 4327844 B2 | 6/2009 |
| JP | 2013-543386 A | 12/2013 |
| WO | WO 01/38523 A1 | 5/2001 |
| WO | WO 2012/002582 A1 | 1/2012 |
| WO | WO 2012/161352 A1 | 11/2012 |

OTHER PUBLICATIONS

Watanabe et al. (Oncology Reports, 2013, vol. 31, p. 1089-1095).*
International Search Report and Written Opinion dated Aug. 25, 2015, in PCT/JP2015/065004.
Choi et al., "Effect of decorin on overcoming the extracellular matrix barrier for oncolytic virotherapy," Gene Therapy, 2010, 17:190-201.
Dave et al., "Viral warfare! Front-line defence and arming the immune system against cancer using oncolytic vaccinia and other viruses," The Surgeon, 2014, 12:210-220.
Gomez-Manzano et al., "A novel E1A-E1B mutant adenovirus induces glioma regression in vivo," Oncogene, 2004, 23:1821-1828.
Kim et al., "Evaluation of E1B gene-attenuated replicating adenovirus for cancer gene therapy," Cancer Gene Therapy, 2002, 9:725-736.
Kim et al., "Ad-mTERT-Δ9, a Conditional Replication—Competent Adenovirus Driven by the Human Telomerase Promoter, Selectively Replicates in and Elicits Cytopathic Effect in a Cancer Cell-Specific Manner," Human Gene Therapy, Oct. 10, 2003, 14:1415-1428.
Kumon, Hiromi, "Gene Therapy for Prostate Cancer: Current Status and Future Prospects," Japanese Journal of Clinical Medicine, 2011, 69(5:Suppl.):544-549, with partial English translation.
Kwon et al., "A Hypoxia- and α-Fetoprotein Dependent Oncolytic Adenovirus Exhibits Specific Killing of Hepatocellular Carcinomas," Clinical Cancer Research, Dec. 15, 2010, 16(24):6071-6082.
Nemunaitis et al., "A Phase I Study of Telomerase-specific Replication Competent Oncolytic Adenovirus (Telomelysin) for Various Solid Tumors," Molecular Therapy, Feb. 2010, 18(2):429-434.

(Continued)

*Primary Examiner* — Agnieszka Boesen
(74) *Attorney, Agent, or Firm* — Foley & Lardner LLP

(57) ABSTRACT

An object of the present invention is to provide a conditionally replicating adenovirus having a strong anticancer effect. A conditionally replicating adenovirus to replicate specifically in a cancer cell and express REIC protein or REIC C domain protein, wherein the conditionally replicating adenovirus is obtained by inserting full-length REIC DNA or REIC C domain DNA into a conditionally replicating adenovirus comprising an ITR (inverted terminal repeat) sequence of an adenovirus type 5 genome and insertion of an HRE sequence, an hTERT promoter, a decorin-encoding DNA, and a DNA encoding a peptide comprising an RGD sequence.

6 Claims, 7 Drawing Sheets
Specification includes a Sequence Listing.

(56) References Cited

OTHER PUBLICATIONS

Parmiani et al., "Opposite immune functions of GM-CSF administered as vaccine adjuvant in cancer patients," Annals of Oncology, 2007, 18:226-232.

Shimazu et al., "Effect of combination therapy of the adenovirus vector carrying REIC/Dkk-3 (Ad-REIC) and the integrin antagonist cRGD," The Japan Society for Neuro-Oncology Program Shorokushi, Dec. 17, 2014, 32:100 ("P-63"), with English translation.

Senzer et al., "Phase II Clinical Trial of a Granulocyte-Macrophage Colony-Stimulating Factor-Encoding, Second-Generation Oncolytic Herpesvirus in Patients with Unresectable Metastatic Melanoma," J. Clin. Oncol., Dec. 1, 2009, 27(34):5763-5771.

Watanabe et al. "Adenovirus-mediated REIC/Dkk-3 gene therapy: Development of an autologous cancer vaccination therapy (Review)," Oncology Letters, 2004, 7:595-601.

Wu et al., "RGD peptide-modified adenovirus expressing hepatocyte growth factor and X-linked inhibitor of apoptosis improves islet transplantation," J. Gene Med., Dec. 2011, 13(12):658-669.

* cited by examiner

Sequence of m-hTERT
Patent : Excerpted from JP Patent No. 4327844

SEQUENCE LISTING

```
<160> NUMBER OF SEQ ID NOS: 14

<210> SEQ ID NO 1
<211> LENGTH: 10
<212> TYPE: DNA
<213> ORGANISM: Artificial
```

```
<220> FEATURE:
<223> OTHER INFORMATION: Synthetic

<400> SEQUENCE: 1
cccccgcccc                                                                10

<210> SEQ ID NO 2
<211> LENGTH: 902
<212> TYPE: DNA
<213> ORGANISM: Artificial
<220> FEATURE:
<223> OTHER INFORMATION: Synthetic

<400> SEQUENCE: 2
agatctctcc gctggggccc tcgctggcgt ccctgcaccc tgggagcgcg agcggcgcgc        60
gggcggggaa gcgcggccca gaccccnggg tccgcccgga gcagctgcgc tgtcggggcc       120
aggccgggct cccagtggat tcgcgggcac agacgcccag gaccgcgctt cccacgtggc       180
ggagggactg gggaccnggg cacccgtcct gcccnttcac cttccagctc cgcctcctcc       240
gcgcggaccc cgccccgtcc cgaccnctcc cgggtccccg gccagccccc ctccgggccc       300
tcccagcccc tccccttcct ttccgcggcc ccgccnctc ctcgcggcgc gagtttcagg        360
cagcgctgcg tcctgctgcg cacgtgggaa gccctggccc cggccacccc cgcgtgaagc       420
ttgcatgcct gcaggtcgac tctagaggat ctactagtca tatggatgag ctcgagctgc       480
accctgggag cgcgagcggc gcgcgggcgg ggaagcgcgg cccagacccc cgggtccgcc       540
cggagcagct gcgctgtcgg ggccaggccg ggctcccagt ggattcgcgg gcacagacgc       600
ccaggaccgc gcttcccacg tggcggaggg actggggacc cggncacccg tcctgcccct       660
tcaccttcca gctccgcctc ctccgcgcgg acccgccc gtcccgaccn ctccgggtc         720 cccggcccag ccccctccgg gccctcccag ccctccccc tcctttccgc ggccccgccc       780
tctcctcgag ctcgagatcg gatcccnggg taccgaggcg aattcggctt ctcgagccac       840
tcttgagtgc agcgagtag agttttctcc tccgagccgc tccgacaccg ggactgaaaa       900
tg                                                                        902

<210> SEQ ID NO 3
<211> LENGTH: 34
<212> TYPE: DNA
<213> ORGANISM: Artificial
<220> FEATURE:
<223> OTHER INFORMATION: Synthetic

<400> SEQUENCE: 3
cacagtgcat acgtgggctc caacaggtcc tctt                                    34

<210> SEQ ID NO 4
<211> LENGTH: 35935
<212> TYPE: DNA
<213> ORGANISM: Human adenovirus 5

<400> SEQUENCE: 4
catcatcaat aatataccct atttttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180 gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
```

```
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa tgagacatat tatctgccac ggaggtgtta ttaccgaaga    600
aatggccgcc agtcttttgg accagctgat cgaagaggta ctggctgata atcttccacc    660
tcctagccat tttgaaccac ctacccttca cgaactgtat gatttagacg tgacggcccc    720
cgaagatccc aacgaggagg cggtttcgca gattttccc gactctgtaa tgttggcggt    780
gcaggaaggg attgacttac tcacttttcc gccggcgccc ggttctccgg agccgcctca    840
cctttcccgg cagcccgagc agccggagca gagagccttg ggtccggttt ctatgccaaa    900
ccttgtaccg gaggtgatcg atcttacctg ccacgaggct ggctttccac ccagtgacga    960
cgaggatgaa gagggtgagg agtttgtgtt agattatgtg gagcacccg ggcacggttg    1020 caggtcttgt cattatcacc ggaggaatac ggggaccca gatattatgt gttcgctttg    1080
ctatatgagg acctgtggca tgtttgtcta cagtaagtga aaattatggg cagtgggtga    1140
tagagtggtg ggtttggtgt ggtaattttt tttttaattt ttacagtttt gtggtttaaa    1200
gaattttgta ttgtgatttt tttaaaaggt cctgtgtctg aacctgagcc tgagcccgag    1260
ccagaaccgg agcctgcaag acctacccgc cgtcctaaaa tggcgcctgc tatcctgaga    1320
cgcccgacat cacctgtgtc tagagaatgc aatagtagta cggatagctg tgactccggt    1380
ccttctaaca cacctcctga gatacacccg gtggtcccgc tgtgccccat taaaccagtt    1440
gccgtgagag ttggtgggcg tcgccaggct gtggaatgta tcgaggactt gcttaacgag    1500
cctgggcaac ctttggactt gagctgtaaa cgccccaggc cataaggtgt aaacctgtga    1560
ttgcgtgtgt ggttaacgcc tttgtttgct gaatgagttg atgtaagttt aataaagggt    1620
gagataatgt ttaacttgca tggcgtgtta aatgggcgg ggcttaaagg gtatataatg    1680
cgccgtgggc taatcttggt tacatctgac ctcatggagg cttgggagtg tttggaagat    1740 tttctgctg tgcgtaactt gctggaacag agctctaaca gtacctcttg gttttggagg    1800
tttctgtggg gctcatccca ggcaaagtta gtctgcagaa ttaaggagga ttacaagtgg    1860 gaattgaag agcttttgaa atcctgtggt gagctgtttg attctttgaa tctgggtcac    1920
caggcgcttt tccaagagaa ggtcatcaag actttggatt tttccacacc ggggcgcgct    1980
gcggctgctg ttgcttttttt gagttttata aaggataaat ggagcgaaga aacccatctg    2040
agcggggggt acctgctgga ttttctggcc atgcatctgt ggagagcggt tgtgagacac    2100
aagaatcgcc tgctactgtt gtcttccgtc cgcccggcga taataccgac ggaggagcag    2160
cagcagcagc aggaggaagc caggcggcgg cggcaggagc agagcccatg gaacccgaga    2220 gccgcctgg accctcggga atgaatgttg tacaggtggc tgaactgtat ccagaactga    2280
gacgcatttt gacaattaca gaggatgggc agggctaaa ggggtaaag agggagcggg    2340 gggcttgtga ggctacagag gaggctagga atctagcttt tagcttaatg accagacacc    2400
gtcctgagtg tattactttt caacagatca aggataattg cgctaatgag cttgatctgc    2460
tggcgcagaa gtattccata gagcagctga ccacttactg gctgcagcca ggggatgatt    2520
ttgaggaggc tattagggta tatgcaaagg tggcacttag gccagattgc aagtacaaga    2580 tcagcaaaact tgtaaatatc aggaattgtt gctacatttc tgggaacggg gccgaggtgc    2640
agatagatac ggaggatagg gtggcctta gatgtagcat gataaatatg tggccgggg     2700
```

-continued

```
tgcttggcat ggacggggtg gttattatga atgtaaggtt tactggcccc aattttagcg    2760
gtacggtttt cctggccaat accaaccttt tcctacacgg tgtaagcttc tatgggttta    2820
acaatacctg tgtggaagcc tggaccgatg taagggttcg gggctgtgcc ttttactgct    2880
gctggaaggg ggtggtgtgt cgccccaaaa gcagggcttc aattaagaaa tgcctctttg    2940
aaaggtgtac cttgggtatc ctgtctgagg gtaactccag ggtgcgccac aatgtggcct    3000
ccgactgtgg ttgcttcatg ctagtgaaaa gcgtggctgt gattaagcat aacatggtat    3060
gtggcaactg cgaggacagg gcctctcaga tgctgacctg ctcggacggc aactgtcacc    3120
tgctgaagac cattcacgta gccagccact ctcgcaaggc ctggccagtg tttgagcata    3180
acatactgac ccgctgttcc ttgcatttgg gtaacaggag gggggtgttc ctaccttacc    3240
aatgcaattt gagtcacact aagatattgc ttgagcccga gagcatgtcc aaggtgaacc    3300
tgaacggggt gtttgacatg accatgaaga tctggaaggt gctgaggtac gatgagaccc    3360
gcaccaggtg cagaccctgc gagtgtggcg gtaaacatat taggaaccag cctgtgatgc    3420
tggatgtgac cgaggagctg aggcccgatc acttggtgct ggcctgcacc cgcgctgagt    3480
ttggctctag cgatgaagat acagattgag gtactgaaat gtgtgggcgt ggcttaaggg    3540
tgggaaagaa tatataaggt gggggtctta tgtagttttg tatctgtttt gcagcagccg    3600
ccgccgccat gagcaccaac tcgtttgatg gaagcattgt gagctcatat ttgacaacgc    3660
gcatgccccc atgggccggg gtgcgtcaga atgtgatggg ctccagcatt gatggtcgcc    3720
ccgtcctgcc cgcaaactct actaccttga cctacgagac cgtgtctgga acgccgttgg    3780
agactgcagc ctccgccgcc gcttcagccg ctgcagccac cgcccgcggg attgtgactg    3840
actttgcttt cctgagcccg cttgcaagca gtgcagcttc ccgttcatcc gcccgcgatg    3900
acaagttgac ggctcttttg gcacaattgg attctttgac ccgggaactt aatgtcgttt    3960
ctcagcagct gttggatctg cgccagcagg tttctgccct gaaggcttcc tcccctccca    4020
atgcggttta aaacataaat aaaaaaccag actctgtttg gatttggatc aagcaagtgt    4080
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320
cttttcagtag caagctgatt gccaggggca ggcccttggt gtaagtgttt acaaagcggt    4380
taagctggga tgggtgcata cgtggggata tgagatgcat cttggactgt attttttaggt   4440
tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggc ggcggcctgg gcgaagatat ttctgggatc actaacgtca tagttgtgtt    4680
ccaggatgag atcgtcatag gccatttttta caaagcgcgg gcggagggtg ccagactgcg    4740
gtataatggt tccatccggc ccaggggcgt agttaccctc acagatttgc atttcccacg    4800
ctttgagttc agatggggggg atcatgtcta cctgcggggc gatgaagaaa acggtttccg    4860
gggtagggga gatcagctgg gaagaaagca ggttcctgag cagctgcgac ttaccgcagc    4920
cggtgggccc gtaaatcaca cctattaccg ggtgcaactg gtagttaaga gagctgcagc    4980
tgccgtcatc cctgagcagg ggggccactt cgttaagcat gtccctgact cgcatgtttt    5040
ccctgaccaa atccgccaga aggcgctcgc cgcccagcga tagcagttct tgcaaggaag    5100
```

```
caaagttttt caacggtttg agaccgtccg ccgtaggcat gcttttgagc gtttgaccaa    5160
gcagttccag gcggtcccac agctcggtca cctgctctac ggcatctcga tccagcatat    5220
ctcctcgttt cgcgggttgg ggcggctttc gctgtacggc agtagtcggt gctcgtccag    5280
acgggccagg gtcatgtctt ccacgggcg cagggtcctc gtcagcgtag tctgggtcac     5340
ggtgaagggg tgcgctccgg gctgcgcgct ggccagggtg cgcttgaggc tggtcctgct    5400
ggtgctgaag cgctgccggt cttcgccctg cgcgtcggcc aggtagcatt tgaccatggt    5460
gtcatagtcc agcccctccg cggcgtggcc cttggcgcgc agcttgccct tggaggaggc    5520
gccgcacgag gggcagtgca gacttttgag ggcgtagagc ttgggcgcga gaaataccga    5580
ttccggggag taggcatccg cgccgcaggc cccgcagacg gtctcgcatt ccacgagcca    5640
ggtgagctct ggccgttcgg ggtcaaaaac caggtttccc ccatgctttt tgatgcgttt    5700
cttacctctg gtttccatga gccggtgtcc acgctcggtg acgaaaaggc tgtccgtgtc    5760
cccgtataca gacttgagag gcctgtcctc gagcggtgtt ccgcggtcct cctcgtatag    5820
aaactcggac cactctgaga caaaggctcg cgtccaggcc agcacgaagg aggctaagtg    5880
ggaggggtag cggtcgttgt ccactagggg gtccactcgc tccagggtgt gaagacacat    5940
gtcgccctct tcggcatcaa ggaaggtgat tggtttgtag gtgtaggcca cgtgaccggg    6000
tgttcctgaa gggggctat aaaaggggt ggggcgcgt tcgtcctcac tctcttccgc       6060
atcgctgtct gcgagggcca gctgttgggg tgagtactcc ctctgaaaag cgggcatgac    6120
ttctgcgcta agattgtcag tttccaaaaa cgaggaggat tgatattca cctggcccgc     6180 ggtgatgcct ttgagggtgg ccgcatccat ctggtcagaa aagacaatct ttttgttgtc    6240
aagcttggtg gcaaacgacc cgtagagggc gttggacagc aacttggcga tggagcgcag    6300
ggtttggttt ttgtcgcgat cggcgcgctc cttggccgcg atgtttagct gcacgtattc    6360
gcgcgcaacg caccgccatt cgggaaagac ggtggtgcgc tcgtcgggca ccaggtgcac    6420
gcgccaaccg cggttgtgca gggtgacaag gtcaacgctg gtggctacct ctccgcgtag   6480
gcgctcgttg gtccagcaga ggcggccgcc cttgcgcgag cagaatggcg gtaggggtc     6540 tagctgcgtc tcgtccgggg ggtctgcgtc cacggtaaag acccccgggca gcaggcgcgc   6600 gtcgaagtag tctatcttgc atccttgcaa gtctagcgcc tgctgccatg cgcgggcggc   6660
aagcgcgcgc tcgtatgggt tgagtggggg accccatggc atgggtgggg tgagcgcgga   6720
ggcgtacatg ccgcaaatgt cgtaaacgta gaggggctct ctgagtattc aagatatgt    6780 agggtagcat cttccaccgc ggatgctggc gcgcacgtaa tcgtatagtt cgtgcgaggg    6840
agcgaggagg tcgggaccga ggttgctacg ggcgggctgc tctgctcgga agactatctg    6900
cctgaagatg gcatgtgagt tggatgatat ggttggacgc tggaagacgt tgaagctggc    6960
gtctgtgaga cctaccgcgt cacgcacgaa ggaggcgtag gagtcgcgca gcttgttgac    7020
cagctcggcg gtgacctgca cgtctagggc gcagtagtcc agggtttcct tgatgatgtc    7080
atacttatcc tgtccctttt ttttccacag ctcgcggttg aggacaaact cttcgcggtc    7140
tttccagtac tcttggatcg gaaacccgtc ggcctccgaa cggtaagagc ctagcatgta    7200
gaactggttg acggcctggt aggcgcagca tccctttct acgggtagcg cgtatgcctg     7260
cgcggccttc cggagcgagg tgtgggtgag cgcaaaggtg tccctgacca tgactttgag    7320
gtactggtat ttgaagtcag tgtcgtcgca tccgccctgc tcccagagca aaaagtccgt    7380 gcgcttttg gaacgcggat ttggcagggc gaaggtgaca tcgttgaaga gtatctttcc     7440
cgcgcgaggc ataaagttgc gtgtgatgcg gaagggtccc ggcacctcgg aacggttgtt    7500
```

```
aattacctgg gcggcgagca cgatctcgtc aaagccgttg atgttgtggc ccacaatgta    7560
aagttccaag aagcgcggga tgcccttgat ggaaggcaat tttttaagtt cctcgtaggt    7620
gagctcttca ggggagctga gcccgtgctc tgaaagggcc cagtctgcaa gatgagggtt    7680
ggaagcgacg aatgagctcc acaggtcacg ggccattagc atttgcaggt ggtcgcgaaa    7740
ggtcctaaac tggcgaccta tggccatttt ttctggggtg atgcagtaga aggtaagcgg    7800
gtcttgttcc cagcggtccc atccaaggtt cgcggctagg tctcgcgcgg cagtcactag    7860
aggctcatct ccgccgaact tcatgaccag catgaagggc acgagctgct tcccaaaggc    7920
ccccatccaa gtataggtct ctacatcgta ggtgacaaag agacgctcgg tgcgaggatg    7980
cgagccgatc gggaagaact ggatctcccg ccaccaattg gaggagtggc tattgatgtg    8040
gtgaaagtag aagtccctgc gacgggccga acactcgtgc tggcttttgt aaaaacgtgc    8100
gcagtactgg cagcggtgca cgggctgtac atcctgcacg aggttgacct gacgaccgcg    8160
cacaaggaag cagagtggga atttgagccc ctcgcctggc gggtttggct ggtggtcttc    8220
tacttcggct gcttgtcctt gaccgtctgg ctgctcgagg ggagttacgg tggatcggac    8280
caccacgccg cgcgagccca aagtccagat gtccgcgcgc ggcggtcgga gcttgatgac    8340
aacatcgcgc agatgggagc tgtccatggt ctggagctcc cgcggcgtca ggtcaggcgg    8400
gagctcctgc aggtttacct cgcatagacg ggtcagggcg cgggctagat ccaggtgata    8460
cctaatttcc aggggctggt tggtggcggc gtcgatggct tgcaagaggc cgcatccccg    8520
cggcgcgact acggtaccgc gcggcgggcg gtgggccgcg ggggtgtcct tggatgatgc    8580
atctaaaagc ggtgacgcgg gcgagccccc ggaggtaggg gggctccgg acccgccggg    8640 agaggggggca ggggcacgtc ggcgccgcgc gcgggcagga gctggtgctg cgcgcgtagg    8700
ttgctggcga acgcgacgac gcggcggttg atctcctgaa tctggcgcct ctgcgtgaag    8760
acgacgggcc cggtgagctt gagcctgaaa gagagttcga cagaatcaat ttcggtgtcg    8820
ttgacggcgc cctggcgcaa aatctcctgc acgtctcctg agttgtcttg ataggcgatc    8880
tcggccatga actgctcgat ctcttcctcc tggagatctc cgcgtccggc tcgctccacg    8940
gtggcggcga ggtcgttgga aatgcgggcc atgagctgcg agaaggcgtt gaggcctccc    9000
tcgttccaga cgcggctgta gaccacgccc ccttcggcat cgcgggcgcg catgaccacc    9060
tgcgcgagat tgagctccac gtgcggggcg aagacggcgt agtttcgcag gcgctgaaag    9120
aggtagttga gggtggtggc ggtgtgttct gccacgaaga agtacataac ccagcgtcgc    9180
aacgtggatt cgttgatatc ccccaaggcc tcaaggcgct ccatggcctc gtagaagtcc    9240
acggcgaagt tgaaaaactg ggagttgcgc gccgacacgg ttaactcctc ctccagaaga    9300
cggatgagct cggcgacagt gtcgcgcacc tcgcgctcaa aggctacagg ggcctcttct    9360
tcttcttcaa tctcctcttc cataagggcc tcccttctt cttcttctgg cggcggtggg    9420 ggaggggggga cacggcggcg acgacggcgc accgggaggc ggtcgacaaa gcgctcgatc    9480
atctccccgc ggcgacggcg catggtctcg gtgacgcgc ggccgttctc gcgggggcgc    9540
agttggaaga cgccgcccgt catgtcccgg ttatgggttg gcgggggggct gccatgcggc    9600 agggatacgg cgctaacgat gcatctcaac aattgttgtg taggtactcc gccgccgagg    9660
gacctgagcg agtccgcatc gaccggatcg gaaaacctct cgagaaaggc gtctaaccag    9720
tcacagtcgc aaggtaggct gagcaccgtg gcggcggca gcggcggcg gtcggggttg    9780 tttctggcga aggtgctgct gatgatgtaa ttaaagtagg cggtcttgag acggcggatg    9840
gtcgacagaa gcaccatgtc cttgggtccg gcctgctgaa tgcgcaggcg gtcggccatg    9900
```

```
ccccaggctt cgttttgaca tcggcgcagg tctttgtagt agtcttgcat gagcctttct    9960
accggcactt cttcttctcc ttcctcttgt cctgcatctc ttgcatctat cgctgcggcg   10020
gcggcggagt ttggccgtag gtggcgccct cttcctccca tgcgtgtgac cccgaagccc   10080
ctcatcggct gaagcagggc taggtcgcg acaacgcgct cggctaatat ggcctgctgc    10140
acctgcgtga gggtagactg gaagtcatcc atgtccacaa agcggtggta tgcgcccgtg   10200
ttgatggtgt aagtgcagtt ggccataacg gaccagttaa cggtctggtg acccggctgc   10260
gagagctcgg tgtacctgag acgcgagtaa gccctcgagt caaatacgta gtcgttgcaa   10320
gtccgcacca ggtactggta tcccaccaaa aagtgcggcg gcggctggcg gtagaggggc   10380
cagcgtaggg tggccggggc tccggggcg agatcttcca acataaggcg atgatatccg    10440
tagatgtacc tggacatcca ggtgatgccg cggcggtgg tggaggcgcg cggaaagtcg    10500
cggacgcggt tccagatgtt gcgcagcggc aaaaagtgct ccatggtcgg gacgctctgg   10560
ccggtcaggc gcgcgcaatc gttgacgctc tagaccgtgc aaaaggagag cctgtaagcg   10620
ggcactcttc cgtggtctgg tggataaatt cgcaagggta tcatggcgga cgaccggggt   10680
tcgagccccg tatccggccg tccgccgtga tccatgcgt taccgcccgc gtgtcgaacc    10740
caggtgtgcg acgtcagaca acgggggagt gctccttttg gcttccttcc aggcgcggcg   10800
gctgctgcgc tagctttttt ggccactggc cgcgcgcagc gtaagcggtt aggctggaaa   10860
gcgaaagcat taagtggctc gctccctgta gccgagggt tattttccaa gggttgagtc    10920
gcgggacccc cggttcgagt ctcggaccgg ccggactgcg gcgaacgggg gtttgcctcc   10980
ccgtcatgca agacccgct tgcaaattcc tccggaaaca gggacgagcc ccttttttgc    11040
ttttcccaga tgcatccggt gctgcggcag atgcgccccc ctcctcagca gcggcaagag   11100
caagagcagc ggcagacatg cagggcaccc tcccctcctc ctaccgcgtc aggaggggcg   11160
acatccgcgg ttgacgcggc agcagatggt gattacgaac cccgcggcg ccgggcccgg    11220
cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtgagcccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccataccct tacgttccca tagacaagga ggtaaagatc    11940
gagggggttct acatgcgcat ggcgctgaag gtgcttacct tgagcgacga cctgggcgtt   12000
tatcgcaacg agcgcatcca aaggccgtg agcgtgagcc ggcggcgcga gctcagcgac    12060
cgcgagctga tgcacagcct gcaaagggcc ctggctggca cgggcagcgg cgatagagag   12120
gccgagtcct actttgacgc gggcgctgac ctgcgctggg ccccaagccg acgcgccctg   12180
gaggcagctg gggccggacc tgggctggcg gtggcacccg cgcgcgctgg caacgtcggc   12240
ggcgtggagg aatatgacga ggacgatgag tacgagccag aggacggcga gtactaagcg   12300
```

```
gtgatgtttc tgatcagatg atgcaagacg caacggaccc ggcggtgcgg gcggcgctgc    12360
agagccagcc gtccggcctt aactccacgg acgactggcg ccaggtcatg gaccgcatca    12420
tgtcgctgac tgcgcgcaat cctgacgcgt tccggcagca gccgcaggcc aaccggctct    12480
ccgcaattct ggaagcggtg gtcccggcgc gcgcaaaccc cacgcacgag aaggtgctgg    12540
cgatcgtaaa cgcgctggcc gaaaacaggg ccatccggcc cgacgaggcc ggcctggtct    12600
acgacgcgct gcttcagcgc gtggctcgtt caacagcgg caacgtgcag accaacctgg    12660
accggctggt gggggatgtg cgcgaggccg tggcgcagcg tgagcgcgcg cagcagcagg    12720
gcaacctggg ctccatggtt gcactaaacg ccttcctgag tacacagccc gccaacgtgc    12780
cgcggggaca ggaggactac accaactttg tgagcgcact gcggctaatg gtgactgaga    12840
caccgcaaag tgaggtgtac cagtctgggc cagactattt tttccagacc agtagacaag    12900
gcctgcagac cgtaaacctg agccaggctt tcaaaaactt gcaggggctg tgggggtgc    12960 gggctcccac aggcgaccgc gcgaccgtgt ctagcttgct gacgcccaac tcgcgcctgt    13020
tgctgctgct aatagcgccc ttcacggaca gtggcagcgt gtcccgggac acatacctag    13080
gtcacttgct gacactgtac cgcgaggcca taggtcaggc gcatgtggac gagcatactt    13140
tccaggagat tacaagtgtc agccgcgcgc tggggcagga ggacacgggc agcctggagg    13200
caaccctaaa ctacctgctg accaaccggc ggcagaagat cccctcgttg cacagtttaa    13260
acagcgagga ggagcgcatt ttgcgctacg tgcagcagag cgtgagcctt aacctgatgc    13320
gcgacggggt aacgcccagc gtggcgctgg acatgaccgc gcgcaacatg gaaccgggca    13380
tgtatgcctc aaaccggccg tttatcaacc gcctaatgga ctacttgcat cgcgcggccg    13440
ccgtgaaccc cgagtatttc accaatgcca tcttgaaccc gcactggcta ccgccccctg    13500
gtttctacac cggggggattc gaggtgcccg agggtaacga tggattcctc tgggacgaca    13560
tagacgacag cgtgttttcc ccgcaaccgc agaccctgct agagttgcaa cagcgcgagc    13620
aggcagaggc ggcgctgcga aaggaaagct tccgcaggcc aagcagcttg tccgatctag    13680
gcgctgcggc cccgcggtca gatgctagta gcccatttcc aagcttgata gggtctctta    13740
ccagcactcg caccacccgc ccgcgcctgc tgggcgagga ggagtaccta aacaactcgc    13800
tgctgcagcc gcagcgcgaa aaaaacctgc ctccggcatt tcccaacaac gggatagaga    13860
gcctagtgga caagatgagt agatggaaga cgtacgcgca ggagcacagg gacgtgccag    13920
gcccgcgccc gcccacccgt cgtcaaaggc acgaccgtca gcggggtctg gtgtgggagg    13980
acgatgactc ggcagacgac agcagcgtcc tggatttggg agggagtggc aacccgtttg    14040
cgcaccttcg ccccaggctg gggagaatgt tttaaaaaaa aaaagcatg atgcaaaata    14100 aaaaactcac caaggccatg gcaccgagcg ttggttttct tgtattcccc ttagtatgcg    14160
gcgcgcggcg atgtatgagg aaggtcctcc tccctcctac gagagtgtgg tgagcgcggc    14220
gccagtggcg gcggcgctgg gttctcccct cgatgctccc ctggaccgcc gtttgtgcc    14280 tccgcggtac ctgcggccta ccgggggggag aaacagcatc cgttactctg agttggcacc    14340
cctattcgac accacccgtg tgtacctggt ggacaacaag tcaacggatg tggcatccct    14400
gaactaccag aacgaccaca gcaactttct gaccacggtc attcaaaaca atgactacag    14460
cccgggggag gcaagcacac agaccatcaa tcttgacgac cggtcgcact ggggcggcga    14520
cctgaaaacc atcctgcata ccaacatgcc aaatgtgaac gagttcatgt ttaccaataa    14580
gtttaaggcg cgggtgatgg tgtcgcgctt gcctactaag acaatcagg tggagctgaa    14640 atacgagtgg gtggagttca cgctgcccga gggcaactac tccgagacca tgaccataga    14700
```

```
ccttatgaac aacgcgatcg tggagcacta cttgaaagtg ggcagacaga acggggttct    14760
ggaaagcgac atcggggtaa agtttgacac ccgcaacttc agactggggt ttgaccccgt    14820
cactggtctt gtcatgcctg ggtatatac aaacgaagcc ttccatccag acatcatttt     14880
gctgccagga tgcggggtgg acttcaccca cagccgcctg agcaacttgt tgggcatccg    14940
caagcggcaa cccttccagg agggctttag gatcacctac gatgatctgg agggtggtaa    15000
cattcccgca ctgttggatg tggacgccta ccaggcgagc ttgaaagatg acaccgaaca    15060
gggcggggt ggcgcaggcg gcagcaacag cagtggcagc ggcgcggaag agaactccaa      15120
cgcggcagcc gcggcaatgc agccggtgga ggacatgaac gatcatgcca ttcgcggcga    15180
caccttttgcc acacgggctg aggagaagcg cgctgaggcc gaagcagcgg ccgaagctgc    15240
cgcccccgct gcgcaacccg aggtcgagaa gcctcagaag aaaccggtga tcaaaccccct    15300
gacagaggac agcaagaaac gcagttacaa cctaataagc aatgacagca ccttcaccca     15360
gtaccgcagc tggtaccttg catacaacta cggcgaccct cagaccggaa tccgctcatg    15420
gaccctgctt tgcactcctg acgtaacctg cggctcggag caggtctact ggtcgttgcc    15480
agacatgatg caagacccccg tgaccttccg ctccacgcgc cagatcagca actttccggt   15540
ggtgggcgcc gagctgttgc ccgtgcactc caagagcttc tacaacgacc aggccgtcta    15600
ctcccaactc atccgccagt ttacctctct gacccacgtg ttcaatcgct ttcccgagaa    15660
ccagatttttg gcgcgcccgc cagccccccac catcaccacc gtcagtgaaa acgttcctgc   15720
tctcacagat cacgggacgc taccgctgcg caacagcatc ggaggagtcc agcgagtgac    15780
cattactgac gccagacgcc gcacctgccc ctacgtttac aaggccctgg gcatagtctc    15840
gccgcgcgtc ctatcgagcc gcacttttttg agcaagcatg tccatcctta tatcgcccag    15900
caataacaca ggctggggcc tgcgcttccc aagcaagatg tttggcgggg ccaagaagcg    15960
ctccgaccaa cacccagtgc gcgtgcgcgg gcactaccgc gcgccctggg gcgcgcacaa    16020
acgcggccgc actgggcgca ccaccgtcga tgacgccatc gacgcggtgg tggaggaggc    16080
gcgcaactac acgcccacgc cgccaccagt gtccacagtg gacgcggcca ttcagaccgt    16140
ggtgcgcgga gcccggcgct atgctaaaat gaagagacgg cggaggcgcg tagcacgtcg    16200
ccaccgccgc cgacccggca ctgccgccca acgcgcggcg gcggccctgc ttaaccgcgc    16260
acgtcgcacc ggccgacggg cggccatgcg ggccgctcga aggctggccg cgggtattgt    16320
cactgtgccc cccaggtcca ggcgacgagc ggccgccgca gcagccgcgg ccattagtgc    16380
tatgactcag ggtcgcaggg gcaacgtgta ttgggtgcgc gactcggtta gcggcctgcg    16440
cgtgcccgtg cgcacccgcc ccccgcgcaa ctagattgca agaaaaaact acttagactc    16500
gtactgttgt atgtatccag cggcggcggc gcgcaacgaa gctatgtcca agcgcaaaat    16560
caaagaagag atgctccagg tcatcgcgcc ggagatctat ggccccccga agaaggaaga    16620
gcaggattac aagccccgaa agctaaagcg ggtcaaaaag aaaaagaaag atgatgatga    16680
tgaacttgac gacgaggtgg aactgctgca cgctaccgcg cccaggcgac gggtacagtg    16740
gaaaggtcga cgcgtaaaac gtgttttgcg accggcacc accgtagtct ttacgcccgg    16800
tgagcgctcc acccgcacct acaagcgcgt gtatgatgag gtgtacggcg acgaggacct    16860
gcttgagcag gccaacgagc gcctcgggga gtttgcctac ggaaagcggc ataaggacat    16920
gctggcgttg ccgctggacg agggcaaccc aacacctagc ctaaagcccg taacactgca    16980
gcaggtgctg cccgcgcttg caccgtccga agaaaagcgc ggcctaaagc gcgagtctgg    17040
tgacttggca cccaccgtgc agctgatggt acccaagcgc cagcgactgg aagatgtctt    17100
```

```
ggaaaaaatg accgtggaac ctgggctgga gcccgaggtc cgcgtgcggc caatcaagca    17160
ggtggcgccg ggactgggcg tgcagaccgt ggacgttcag atacccacta ccagtagcac    17220
cagtattgcc accgccacag agggcatgga gacacaaacg tccccggttg cctcagcggt    17280
ggcggatgcc gcggtgcagg cggtcgctgc ggccgcgtcc aagacctcta cggaggtgca    17340
aacggacccg tggatgtttc gcgtttcagc ccccggcgc ccgcgcggtt cgaggaagta    17400
cggcgccgcc agcgcgctac tgcccgaata tgccctacat ccttccattg cgcctacccc    17460
cggctatcgt ggctacacct accgcccag aagacgagca actacccgac gccgaaccac    17520
cactggaacc cgccgccgcc gtcgccgtcg ccagcccgtg ctggcccga tttccgtgcg    17580 cagggtggct cgcgaaggag gcaggaccct ggtgctgcca acagcgcgct accaccccag    17640
catcgtttaa aagccggtct tgtggttct tgcagatatg gccctcacct gccgcctccg    17700
tttcccggtg ccgggattcc gaggaagaat gcaccgtagg aggggcatgg ccggccacgg    17760
cctgacgggc ggcatgcgtc gtgcgcacca ccggcggcgg cgcgcgtcgc accgtcgcat    17820
gcgcggcggt atcctgcccc tccttattcc actgatcgcc gcggcgattg gcgccgtgcc    17880
cggaattgca tccgtggcct tgcaggcgca gagacactga ttaaaaacaa gttgcatgtg    17940
gaaaaatcaa aataaaaagt ctggactctc acgctcgctt ggtcctgtaa ctattttgta    18000
gaatggaaga catcaacttt gcgtctctgg ccccgcgaca cggctcgcgc ccgttcatgg    18060
gaaactggca agatatcggc accagcaata tgagcggtgg cgccttcagc tggggctcgc    18120
tgtggagcgg cattaaaaat ttcggttcca ccgttaagaa ctatggcagc aaggcctgga    18180
acagcagcac aggccagatg ctgagggata agttgaaaga gcaaaatttc caacaaaagg    18240
tggtagatgg cctggcctct ggcattagcg gggtggtgga cctggccaac caggcagtgc    18300
aaaataagat taacagtaag cttgatcccc gccctcccgt agaggagcct ccaccggccg    18360
tggagacagt gtctccagag gggcgtggcg aaaagcgtcc gcgccccgac agggaagaaa    18420
ctctggtgac gcaaatagac gagcctccct cgtacgagga ggcactaaag caaggcctgc    18480
ccaccacccg tcccatcgcg cccatggcta ccggagtgct gggccagcac acacccgtaa    18540
cgctggacct gcctccccccc gccgacaccc agcagaaacc tgtgctgcca ggcccgaccg    18600
ccgttgttgt aaccccgtcct agccgcgcgt ccctgcgccg cgccgccagc ggtccgcgat    18660
cgttgcggcc cgtagccagt ggcaactggc aaagcacact gaacagcatc gtgggtctgg    18720
gggtgcaatc cctgaagcgc cgacgatgct tctgaatagc taacgtgtcg tatgtgtgtc    18780
atgtatgcgt ccatgtcgcc gccagaggag ctgctgagcc gccgcgcgcc cgctttccaa    18840
gatggctacc ccttcgatga tgccgcagtg gtcttacatg cacatctcgg gccaggacgc    18900
ctcggagtac ctgagcccg ggctggtgca gtttgcccgc gccaccgaga cgtacttcag    18960
cctgaataac aagtttagaa accccacggt ggcgcctacg cacgacgtga ccacagaccg    19020
gtcccagcgt ttgacgctgc ggttcatccc tgtggaccgt gaggatactg cgtactcgta    19080
caaggcgcgg ttcaccctag ctgtgggtga taaccgtgtg ctggacatgg cttccacgta    19140
ctttgacatc cgcggcgtgc tggacagggg ccctactttt aagccctact ctggcactgc    19200
ctacaacgcc ctggctccca agggtgcccc aaatccttgc gaatgggatg aagctgctac    19260
tgctcttgaa ataaacctag aagaagagga cgatgacaac gaagacgaag tagacgagca    19320
agctgagcag caaaaaactc acgtatttgg gcaggcgcct tattctggta taaatattac    19380
aaaggagggt attcaaatag gtgtcgaagg tcaaacacct aaatatgccg ataaaacatt    19440
tcaacctgaa cctcaaatag gagaatctca gtggtacgaa actgaaatta atcatgcagc    19500
```

```
tgggagagtc cttaaaaaga ctaccccaat gaaaccatgt tacggttcat atgcaaaacc    19560
cacaaatgaa aatggagggc aaggcattct tgtaaagcaa caaatggaaa agctagaaag    19620
tcaagtggaa atgcaatttt tctcaactac tgaggcgacc gcaggcaatg gtgataactt    19680
gactcctaaa gtggtattgt acagtgaaga tgtagatata gaaacccag acactcatat     19740 ttcttacatg cccactatta aggaaggtaa ctcacgagaa ctaatgggcc aacaatctat    19800
gcccaacagg cctaattaca ttgcttttag ggacaatttt attggtctaa tgtattacaa    19860
cagcacgggt aatatgggtg ttctggcggg ccaagcatcg cagttgaatg ctgttgtaga    19920
tttgcaagac agaaacacag agctttcata ccagcttttg cttgattcca ttggtgatag    19980
aaccaggtac ttttctatgt ggaatcaggc tgttgacagc tatgatccag atgttagaat    20040
tattgaaaat catggaactg aagatgaact tccaaattac tgctttccac tgggaggtgt    20100
gattaataca gagactctta ccaaggtaaa acctaaaaca ggtcaggaaa atggatggga    20160
aaaagatgct acagaatttt cagataaaaa tgaaataaga gttggaaata attttgccat    20220
ggaaatcaat ctaaatgcca acctgtggag aaatttcctg tactccaaca tagcgctgta    20280
tttgcccgac aagctaaagt acagtccttc caacgtaaaa atttctgata acccaaacac    20340
ctacgactac atgaacaagc gagtggtggc tcccgggtta gtggactgct acattaacct    20400
tggagcacgc tggtcccttg actatatgga caacgtcaac ccatttaacc accaccgcaa    20460
tgctggcctg cgctaccgct caatgttgct ggcaatggt cgctatgtgc ccttccacat    20520
ccaggtgcct cagaagttct ttgccattaa aaacctcctt ctcctgccgg gctcatacac    20580
ctacgagtgg aacttcagga aggatgttaa catggttctg cagagctccc taggaaatga    20640
cctaagggtt gacggagcca gcattaagtt tgatagcatt tgcctttacg ccaccttctt    20700
ccccatggcc cacaacaccg cctccacgct tgaggccatg cttagaaacg acaccaacga    20760
ccagtccttt aacgactatc tctccgccgc caacatgctc taccctatac ccgccaacgc    20820
taccaacgtg cccatatcca tcccctcccg caactgggcg ctttccgcg ctgggccttt     20880 cacgcgcctt aagactaagg aaaccccatc actgggctcg gctacgacc cttattacac     20940 ctactctggc tctataccct acctagatgg aacctttac ctcaaccaca cctttaagaa      21000
ggtggccatt accttgact cttctgtcag ctggcctggc aatgaccgcc tgcttacccc      21060
caacgagttt gaaattaagc gctcagttga cggggagggt tacaacgttg cccagtgtaa    21120
catgaccaaa gactggttcc tggtacaaat gctagctaac tacaacattg ctaccaggg      21180 cttctatatc ccagagagct acaaggaccg catgtactcc ttctttagaa acttccagcc    21240
catgagccgt caggtggtgg atgatactaa atacaaggac taccaacagg tgggcatcct    21300
acaccaacac aacaactctg gatttgttgg ctaccttgcc cccaccatgc gcgaaggaca    21360
ggcctaccct gctaacttcc cctatccgct tataggcaag accgcagttg acagcattac    21420
ccagaaaaag tttctttgcg atcgcaccct ttggcgcatc ccattctcca gtaactttat    21480
gtccatgggc gcactcacag acctgggcca aaaccttctc tacgccaact ccgcccacgc    21540
gctagacatg acttttgagg tggatcccat ggacgagccc accctctttt atgttttgtt    21600
tgaagtcttt gacgtggtcc gtgtgcaccg gccgcaccgc ggcgtcatcg aaaccgtgta    21660
cctgcgcacg cccttctcgg ccggcaacgc cacaacataa agaagcaagc aacatcaaca    21720
acagctgccg ccatgggctc cagtgagcag gaactgaaag ccattgtcaa agatcttggt    21780
tgtgggccat atttttgggg cacctatgac aagcgctttc caggctttgt ttctccacac    21840
aagctcgcct gcgccatagt caatacggcc ggtcgcgaga ctggggcgt acactggatg     21900
```

```
gcctttgcct ggaacccgca ctcaaaaaca tgctacctct ttgagccctt tggcttttct   21960
gaccagcgac tcaagcaggt ttaccagttt gagtacgagt cactcctgcg ccgtagcgcc   22020
attgcttctt cccccgaccg ctgtataacg ctggaaaagt ccacccaaag cgtacagggg   22080
cccaactcgg ccgcctgtgg actattctgc tgcatgtttc tccacgcctt tgccaactgg   22140
ccccaaactc ccatggatca aaccccacc atgaaccta ttaccggggt acccaactcc   22200
atgctcaaca gtccccaggt acagcccacc ctgcgtcgca accaggaaca gctctacagc   22260
ttcctggagc gccactcgcc ctacttccgc agccacagtg cgcagattag gagcgccact   22320 tcttttgtc acttgaaaaa catgtaaaaa taatgtacta gagacacttt caataaaggc   22380
aaatgctttt atttgtacac tctcgggtga ttatttaccc ccaccttgc cgtctgcgcc   22440 gtttaaaaat caaggggtt ctgccgcgca tcgctatgcg ccactggcag ggacacgttg   22500
cgatactggt gtttagtgct ccacttaaac tcaggcacaa ccatccgcgg cagctcggtg   22560
aagttttcac tccacaggct gcgcaccatc accaacgcgt ttagcaggtc gggcgccgat   22620
atcttgaagt cgcagttggg gcctccgccc tgcgcgcgcg agttgcgata cacagggttg   22680
cagcactgga acactatcag cgccgggtgg tgcacgctgg ccagcacgct cttgtcggag   22740
atcagatccg cgtccaggtc ctccgcgttg ctcagggcga acggagtcaa ctttggtagc   22800
tgccttccca aaagggcgc gtgcccaggc tttgagttgc actcgcaccg tagtggcatc   22860
aaaaggtgac cgtgcccggt ctgggcgtta ggatacagcg cctgcataaa gccttgatc   22920 tgcttaaaag ccacctgagc ctttgcgcct tcagagaaga acatgccgca agacttgccg   22980
gaaaactgat tggccggaca ggccgcgtcg tgcacgcagc accttgcgtc ggtgttggag   23040
atctgcacca catttcggcc ccaccggttc ttcacgatct tggccttgct agactgctcc   23100
ttcagcgcgc gctgccgtt ttcgctcgtc acatccattt caatcacgtg ctccttattt   23160
atcataatgc ttccgtgtag acacttaagc tcgccttcga tctcagcgca gcggtgcagc   23220
cacaacgcgc agcccgtggg ctcgtgatgc ttgtaggtca cctctgcaaa cgactgcagg   23280
tacgcctgca ggaatcgccc catcatcgtc acaaaggtct tgttgctggt gaaggtcagc   23340
tgcaacccgc ggtgctcctc gttcagccag gtcttgcata cggccgccag agcttccact   23400
tggtcaggca gtagtttgaa gttcgccttt agatcgttat ccacgtggta cttgtccatc   23460
agcgcgcgcg cagcctccat gcccttctcc cacgcagaca cgatcggcac actcagcggg   23520
ttcatcaccg taatttcact ttccgcttcg ctgggctctt cctcttcctc ttgcgtccgc   23580
ataccacgcg ccactgggtc gtcttcattc agccgccgca ctgtgcgctt acctcctttg   23640
ccatgcttga ttagcaccgg tgggttgctg aaacccacca tttgtagcgc cacatcttct   23700
ctttcttcct cgctgtccac gattacctct ggtgatggcg ggcgctcggg cttgggagaa   23760
gggcgcttct ttttcttctt gggcgcaatg gccaaatccg ccgccgaggt cgatggccgc   23820
gggctgggtg tgcgcggcac cagcgcgtct tgtgatgagt cttcctcgtc ctcggactcg   23880
atacgccgcc tcatccgctt ttttggggc gcccggggag gcggcggcga cggggacggg   23940
gacgacacgt cctccatggt tggggacgt cgcgccgcac cgcgtccgcg ctcggggtg   24000 gtttcgcgct gctcctcttc ccgactggcc atttccttct cctataggca gaaaaagatc   24060
atggagtcag tcgagaagaa ggacagccta accgccccct ctgagttcgc caccaccgcc   24120
tccaccgatg ccgccaacgc gcctaccacc ttccccgtcg aggcacccc gcttgaggag   24180 gaggaagtga ttatcgagca ggacccaggt tttgtaagcg aagacgacga ggaccgctca   24240
gtaccaacag aggataaaaa gcaagaccag gacaacgcag aggcaaacga ggaacaagtc   24300
```

```
gggcgggggg acgaaaggca tggcgactac ctagatgtgg gagacgacgt gctgttgaag    24360
catctgcagc gccagtgcgc cattatctgc gacgcgttgc aagagcgcag cgatgtgccc    24420
ctcgccatag cggatgtcag ccttgcctac gaacgccacc tattctcacc gcgcgtaccc    24480
cccaaacgcc aagaaaacgg cacatgcgag cccaacccgc gcctcaactt ctaccccgta    24540
tttgccgtgc cagaggtgct tgccacctat cacatctttt tccaaaactg caagataccc    24600
ctatcctgcc gtgccaaccg cagccgagcg gacaagcagc tggccttgcg gcagggcgct    24660
gtcatacctg atatcgcctc gctcaacgaa gtgccaaaaa tctttgaggg tcttggacgc    24720
gacgagaagc gcgcggcaaa cgctctgcaa caggaaaaca gcgaaaatga aagtcactct    24780
ggagtgttgg tggaactcga gggtgacaac gcgcgcctag ccgtactaaa acgcagcatc    24840
gaggtcaccc actttgccta cccggcactt aacctacccc ccaaggtcat gagcacagtc    24900
atgagtgagc tgatcgtgcg ccgtgcgcag ccctggaga gggatgcaaa tttgcaagaa    24960
caaacagagg agggcctacc cgcagttggc gacgagcagc tagcgcgctg gcttcaaacg    25020
cgcgagcctg ccgacttgga ggagcgacgc aaactaatga tggccgcagt gctcgttacc    25080
gtggagcttg agtgcatgca gcggttcttt gctgacccgg agatgcagcg caagctagag    25140
gaaacattgc actacacctt tcgacagggc tacgtacgcc aggcctgcaa gatctccaac    25200
gtggagctct gcaacctggt ctcctacctt ggaattttgc acgaaaaccg ccttgggcaa    25260
aacgtgcttc attccacgct caagggcgag gcgcgccgcg actacgtccg cgactgcgtt    25320
tacttatttc tatgctacac ctggcagacg gccatgggcg tttggcagca gtgcttggag    25380
gagtgcaacc tcaaggagct gcagaaactg ctaaagcaaa acttgaagga cctatggacg    25440
gccttcaacg agcgctccgt ggccgcgcac ctggcggaca tcatttttccc cgaacgcctg    25500 cttaaaaccc tgcaacaggg tctgccgagac ttcaccagtc aaagcatgtt gcagaacttt    25560
aggaacttta tcctagagcg ctcaggaatc ttgcccgcca cctgctgtgc acttcctagc    25620
gactttgtgc ccattaagta ccgcgaatgc cctccgccgc tttggggcca ctgctacctt    25680
ctgcagctag ccaactacct tgcctaccac tctgacataa tggaagacgt gagcggtgac    25740
ggtctactgg agtgtcactg tcgctgcaac ctatgcaccc cgcaccgctc cctggtttgc    25800
aattcgcagc tgcttaacga aagtcaaatt atcggtacct ttgagctgca gggtcctcg    25860 cctgacgaaa agtccgcggc tccggggttg aaactcactc cggggctgtg gacgtcggct    25920
taccttcgca aatttgtacc tgaggactac cacgcccacg agattaggtt ctacgaagac    25980
caatcccgcc cgccaaatgc ggagcttacc gcctgcgtca ttacccaggg ccacattctt    26040
ggccaattgc aagccatcaa caaagcccgc caagagtttc tgctacgaaa gggacggggg    26100
gtttacttgg accccagtc cggcgaggag ctcaacccaa tcccccgcc gccgcagccc    26160 tatcagcagc agccgcgggc ccttgcttcc caggatggca cccaaaaaga agctgcagct    26220
gccgccgcca cccacggacg aggaggaata ctgggacagt caggcagagg aggttttgga    26280
cgaggaggag gaggacatga tggaagactg ggagagccta gacgaggaag cttccgaggt    26340
cgaagaggtg tcagacgaaa caccgtcacc ctcggtcgca ttcccctcgc cggcgcccca    26400
gaaatcggca accggttcca gcatggctac aacctccgct cctcaggcgc cgccggcact    26460
gcccgttcgc cgacccaacc gtagatggga caccactgga accagggccg gtaagtccaa    26520
gcagccgccg ccgttagccc aagagcaaca acagcgccaa ggctaccgct catggcgcgg    26580
gcacaagaac gccatagttg cttgcttgca agactgtggg ggcaacatct ccttcgcccg    26640
ccgcttcctt ctctaccatc acggcgtggc cttccccgt aacatcctgc attactaccg    26700
```

```
tcatctctac agcccatact gcaccggcgg cagcggcagc ggcagcaaca gcagcggcca    26760
cacagaagca aaggcgaccg gatagcaaga ctctgacaaa gcccaagaaa tccacagcgg    26820
cggcagcagc aggaggagga gcgctgcgtc tggcgcccaa cgaacccgta tcgacccgcg    26880
agcttagaaa caggattttt cccactctgt atgctatatt tcaacagagc aggggccaag    26940
aacaagagct gaaaataaaa aacaggtctc tgcgatccct cacccgcagc tgcctgtatc    27000
acaaaagcga agatcagctt cggcgcacgc tggaagacgc ggaggctctc ttcagtaaat    27060
actgcgcgct gactcttaag gactagtttc gcgcccttc tcaaatttaa gcgcgaaaac     27120
tacgtcatct ccagcggcca cacccggcgc cagcacctgt cgtcagcgcc attatgagca    27180
aggaaattcc cacgccctac atgtggagtt accagccaca aatgggactt gcggctggag    27240
ctgcccaaga ctactcaacc cgaataaact acatgagcgc gggacccac atgatatccc     27300 gggtcaacgg aatccgcgcc caccgaaacc gaattctctt ggaacaggcg gctattacca    27360
ccacacctcg taataacctt aatccccgta gttggcccgc tgccctggtg taccaggaaa    27420
gtcccgctcc caccactgtg gtacttccca gagacgccca ggccgaagtt cagatgacta    27480
actcaggggc gcagcttgcg ggcggctttc gtcacagggt gcggtcgccc gggcagggta    27540
taactcacct gacaatcaga gggcgaggta ttcagctcaa cgacgagtcg gtgagctcct    27600
cgcttggtct ccgtccggac gggacatttc agatcggcgg cgccggccgt ccttcattca    27660
cgcctcgtca ggcaatccta actctgcaga cctcgtcctc tgagccgcgc tctggaggca    27720
ttggaactct gcaatttatt gaggagtttg tgccatcggt ctactttaac cccttctcgg    27780
gacctcccgg ccactatccg gatcaattta ttcctaactt tgacgcggta aaggactcgg    27840
cggacggcta cgactgaatg ttaagtggag aggcagagca actgcgcctg aaacacctgg    27900
tccactgtcg ccgccacaag tgctttgccc gcgactccgg tgagttttgc tactttgaat    27960
tgcccgagga tcatatcgag ggcccggcgc acggcgtccg gcttaccgcc cagggagagc    28020
ttgcccgtag cctgattcgg gagtttaccc agcgccccct gctagttgag cgggacaggg    28080
gaccctgtgt tctcactgtg atttgcaact gtcctaacct tggattacat caagatcttt    28140
gttgccatct ctgtgctgag tataataaat acagaaatta aaatatactg gggctcctat    28200
cgccatcctg taaacgccac cgtcttcacc cgcccaagca aaccaaggcg aaccttacct    28260 ggtacttta acatctctcc ctctgtgatt tacaacagtt tcaacccaga cggagtgagt     28320
ctacgagaga acctctccga gctcagctac tccatcagaa aaacaccac cctccttacc     28380 tgccgggaac gtacgagtgc gtcaccggcc gctgcaccac acctaccgcc tgaccgtaaa    28440
ccagactttt tccggacaga cctcaataac tctgtttacc agaacaggag gtgagcttag    28500 aaaacccta gggtattagg ccaaaggcgc agctactgtg gggtttatga acaattcaag     28560
caactctacg ggctattcta attcaggttt ctctagaatc ggggttgggg ttattctctg    28620
tcttgtgatt ctctttattc ttatactaac gcttctctgc ctaaggctcg ccgcctgctg    28680
tgtgcacatt tgcatttatt gtcagctttt taaacgctgg ggtcgccacc caagatgatt    28740
aggtacataa tcctaggttt actcacccit gcgtcagccc acggtaccac ccaaaaggtg    28800 gatttt aagg agccagcctg taatgttaca ttcgcagctg aagctaatga gtgcaccact    28860
cttataaaat gcaccacaga acatgaaaag ctgcttattc gccacaaaaa caaaattggc    28920
aagtatgctg tttatgctat ttggcagcca ggtgacacta cagagtataa tgttacagtt    28980
ttccagggta aaagtcataa aacttttatg tatacttttc catttt atga aatgtgcgac    29040 attaccatgt acatgagcaa acagtataag ttgtggcccc cacaaaattg tgtggaaaac    29100
```

```
actggcactt tctgctgcac tgctatgcta attacagtgc tcgctttggt ctgtacccta    29160
ctctatatta aatacaaaag cagacgcagc tttattgagg aaaagaaaat gccttaattt    29220
actaagttac aaagctaatg tcaccactaa ctgctttact cgctgcttgc aaaacaaatt    29280
caaaaagtta gcattataat tagaatagga tttaaacccc ccggtcattt cctgctcaat    29340
accattcccc tgaacaattg actctatgtg ggatatgctc cagcgctaca accttgaagt    29400
caggcttcct ggatgtcagc atctgacttt ggccagcacc tgtcccgcgg atttgttcca    29460
gtccaactac agcgacccac cctaacagag atgaccaaca caaccaacgc ggccgccgct    29520
accggactta catctaccac aaatacaccc caagtttctg cctttgtcaa taactgggat    29580
aacttgggca tgtggtggtt ctccatagcg cttatgtttg tatgccttat tattatgtgg    29640
ctcatctgct gcctaaagcg caaacgcgcc cgaccaccca tctatagtcc catcattgtg    29700
ctacacccaa acaatgatgg aatccataga ttggacggac tgaaacacat gttcttttct    29760
cttacagtat gattaaatga gacatgattc ctcgagtttt tatattactg acccttgttg    29820
cgcttttttg tgcgtgctcc acattggctg cggtttctca catcgaagta gactgcattc    29880
cagccttcac agtctatttg ctttacggat ttgtcaccct cacgctcatc tgcagcctca    29940
tcactgtggt catcgccttt atccagtgca ttgactgggc tgtgtgcgc tttgcatatc    30000 tcagacacca tcccccagtac agggacagga ctatagctga gcttcttaga attctttaat    30060
tatgaaattt actgtgactt ttctgctgat tatttgcacc ctatctgcgt tttgttcccc    30120
gacctccaag cctcaaagac atatatcatg cagattcact cgtatatgga atattccaag    30180
ttgctacaat gaaaaaagcg atcttccga agcctggtta tatgcaatca tctctgttat    30240
ggtgttctgc agtaccatct tagccctagc tatatatccc taccttgaca ttggctggaa    30300
acgaatagat gccatgaacc acccaacttt ccccgcgccc gctatgcttc cactgcaaca    30360
agttgttgcc ggcggctttg tcccagccaa tcagcctcgc cccacttctc cacccccac    30420 tgaaatcagc tactttaatc taacaggagg agatgactga cacctagat ctagaaatgg    30480 acggaattat tacagagcag cgcctgctag aaagacgcag ggcagcggcc gagcaacagc    30540
gcatgaatca agagctccaa gacatggtta acttgcacca gtgcaaaagg ggtatcttt    30600 gtctggtaaa gcaggccaaa gtcacctacg acagtaatac caccggacac cgccttagct    30660
acaagttgcc aaccaagcgt cagaaattgg tggtcatggt gggagaaaag cccattacca    30720
taactcagca ctcggtagaa accgaaggct gcattcactc accttgtcaa ggacctgagg    30780
atctctgcac ccttattaag accctgtgcg gtctcaaaga tcttattccc tttaactaat    30840 aaaaaaaat aataaagcat cacttactta aaatcagtta gcaaatttct gtccagttta    30900
ttcagcagca cctccttgcc ctcctcccag ctctggtatt gcagcttcct cctggctgca    30960
aactttctcc acaatctaaa tggaatgtca gtttcctcct gttcctgtcc atccgcaccc    31020
actatcttca tgttgttgca gatgaagcgc gcaagaccgt ctgaagatac cttcaaccc    31080 gtgtatccat atgacacgga aaccggtcct ccaactgtgc ctttcttac tcctcccttt    31140 gtatccccca tgggttttca agagagtccc cctggggtac tctctttgcg cctatccgaa    31200
cctctagtta cctccaatgg catgcttgcg ctcaaaatgg gcaacggcct ctctctggac    31260
gaggccggca accttacctc ccaaaatgta accactgtga gcccacctct caaaaaaacc    31320
aagtcaaaca taaacctgga aatatctgca cccctcacag ttacctcaga agccctaact    31380
gtggctgccg ccgcacctct aatggtcgcg ggcaacacac tcaccatgca atcacaggcc    31440
ccgctaaccg tgcacgactc caaacttagc attgccaccc aaggaccct cacagtgtca    31500
```

```
gaaggaaagc tagccctgca acatcaggc cccctcacca ccaccgatag cagtacccett  31560 actatcactg cctcacccc tctaactact gccactggta gcttgggcat tgacttgaaa  31620
gagcccattt atacacaaaa tggaaaacta ggactaaagt acggggctcc tttgcatgta  31680
acagacgacc taaacacttt gaccgtagca actggtccag gtgtgactat taataatact  31740
tccttgcaaa ctaaagttac tggagccttg ggttttgatt cacaaggcaa tatgcaactt  31800
aatgtagcag gaggactaag gattgattct caaaacagac gccttatact tgatgttagt  31860
tatccgtttg atgctcaaaa ccaactaaat ctaagactag gacagggccc tcttttata   31920 aactcagccc acaacttgga tattaactac aacaaaggcc tttacttgtt tacagcttca  31980
aacaattcca aaagcttga ggttaaccta agcactgcca aggggttgat gtttgacgct  32040
acagccatag ccattaatgc aggagatggg cttgaatttg gttcacctaa tgcaccaaac  32100
acaaatcccc tcaaaacaaa aattggccat ggcctagaat ttgattcaaa caaggctatg  32160
gttcctaaac taggaactgg ccttagtttt gacagcacag gtgccattac agtaggaaac  32220
aaaaataatg ataagctaac tttgtggacc acaccagctc catctcctaa ctgtagacta  32280
aatgcagaga aagatgctaa actcactttg gtcttaacaa aatgtggcag tcaaatactt  32340
gctacagttt cagttttggc tgttaaaggc agtttggctc caatatctgg aacagttcaa  32400
agtgctcatc ttattataag atttgacgaa aatggagtgc tactaaacaa ttccttcctg  32460
gacccagaat attggaactt tagaaatgga gatcttactg aaggcacagc ctatacaaac  32520
gctgttggat ttatgcctaa cctatcagct tatccaaaat ctcacggtaa aactgccaaa  32580
agtaacattg tcagtcaagt ttacttaaac ggagacaaaa ctaaacctgt aacactaacc  32640
attacactaa acggtacaca ggaaacagga gacacaactc caagtgcata ctctatgtca  32700
ttttcatggg actggtctgg ccacaactac attaatgaaa tatttgccac atcctcttac  32760 acttttcat acattgccca agaataaaga atcgtttgtg ttatgtttca acgtgtttat  32820
ttttcaattg cagaaaattt caagtcattt ttcattcagt agtatagccc caccaccaca  32880
tagcttatac agatcaccgt accttaatca aactcacaga accctagtat tcaacctgcc  32940
acctccctcc caacacacag agtacacagt cctttctccc cggctggcct taaaaagcat  33000
catatcatgg gtaacagaca tattcttagg tgttatattc cacacggttt cctgtcgagc  33060
caaacgctca tcagtgatat taataaactc cccgggcagc tcacttaagt tcatgtcgct  33120
gtccagctgc tgagccacag gctgctgtcc aacttgcggt tgcttaacgg gcggcgaagg  33180
agaagtccac gcctacatgg gggtagagtc ataatcgtgc atcaggatag ggcggtggtg  33240
ctgcagcagc gcgcgaataa actgctgccg ccgccgctcc gtcctgcagg aatacaacat  33300
ggcagtggtc tcctcagcga tgattcgcac cgcccgcagc ataaggcgcc ttgtcctccg  33360
ggcacagcag cgcaccctga tctcacttaa atcagcacag taactgcagc acagcaccac  33420
aatattgttc aaaatcccac agtgcaaggc gctgtatcca agctcatgg cggggaccac  33480 agaacccacg tggccatcat accacaagcg caggtagatt aagtggcgac ccctcataaa  33540
cacgctggac ataaacatta cctcttttgg catgttgtaa ttcaccacct cccggtacca  33600
tataaacctc tgattaaaca tggcgccatc caccaccatc ctaaaccagc tggccaaaac  33660
ctgcccgccg gctatacact gcagggaacc gggactggaa caatgacagt ggagagccca  33720
ggactcgtaa ccatggatca tcatgctcgt catgatatca atgttggcac aacacaggca  33780
cacgtgcata cacttcctca ggattacaag ctcctcccgc gttagaacca tatcccaggg  33840
aacaacccat tcctgaatca gcgtaaatcc cacactgcag ggaagacctc gcacgtaact  33900
```

-continued

| | |
|---|---|
| cacgttgtgc attgtcaaag tgttacattc gggcagcagc ggatgatcct ccagtatggt | 33960 |
| agcgcgggtt tctgtctcaa aaggaggtag acgatcccta ctgtacgag tgcgccgaga | 34020 |
| caaccgagat cgtgttggtc gtagtgtcat gccaaatgga acgccggacg tagtcatatt | 34080 |
| tcctgaagca aaaccaggtg cgggcgtgac aaacagatct gcgtctccgg tctcgccgct | 34140 |
| tagatcgctc tgtgtagtag ttgtagtata tccactctct caaagcatcc aggcgccccc | 34200 |
| tggcttcggg ttctatgtaa actccttcat gcgccgctgc cctgataaca tccaccaccg | 34260 |
| cagaataagc cacacccagc caacctacac attcgttctg cgagtcacac acgggaggag | 34320 |
| cgggaagagc tggaagaacc atgttttttt ttttattcca aaagattatc caaaacctca | 34380 |
| aaatgaagat ctattaagtg aacgcgctcc cctccggtgg cgtggtcaaa ctctacagcc | 34440 |
| aaagaacaga taatggcatt tgtaagatgt tgcacaatgg cttccaaaag gcaaacggcc | 34500 |
| ctcacgtcca agtggacgta aaggctaaac ccttcagggt gaatctcctc tataaacatt | 34560 |
| ccagcacctt caaccatgcc caaataattc tcatctcgcc accttctcaa tatatctcta | 34620 |
| agcaaatccc gaatattaag tccggccatt gtaaaaatct gctccagagc gccctccacc | 34680 |
| ttcagcctca agcagcgaat catgattgca aaaattcagg ttcctcacag acctgtataa | 34740 |
| gattcaaaag cggaacatta acaaaaatac cgcgatcccg taggtccctt cgcagggcca | 34800 |
| gctgaacata atcgtgcagg tctgcacgga ccagcgcggc cacttccccg ccaggaacct | 34860 |
| tgacaaaaga acccacactg attatgacac gcatactcgg agctatgcta accagcgtag | 34920 |
| ccccgatgta agctttgttg catgggcggc gatataaaat gcaaggtgct gctcaaaaaa | 34980 |
| tcaggcaaag cctcgcgcaa aaagaaagc acatcgtagt catgctcatg cagataaagg | 35040 |
| caggtaagct ccggaaccac cacagaaaaa gacaccattt ttctctcaaa catgtctgcg | 35100 |
| ggtttctgca taaacacaaa ataaaataac aaaaaaacat ttaaacatta gaagcctgtc | 35160 |
| ttacaacagg aaaaacaacc cttataagca taagacggac tacggccatg ccggcgtgac | 35220 |
| cgtaaaaaaa ctggtcaccg tgattaaaaa gcaccaccga cagctcctcg gtcatgtccg | 35280 |
| gagtcataat gtaagactcg gtaaacacat caggttgatt catcggtcag tgctaaaaag | 35340 |
| cgaccgaaat agcccggggg aatacatacc cgcaggcgta gagacaacat tacagccccc | 35400 |
| ataggaggta taacaaaatt aataggagag aaaaacacat aaacacctga aaaccctcc | 35460 |
| tgcctaggca aaatagcacc ctcccgctcc agaacaacat acagcgcttc acagcggcag | 35520 |
| cctaacagtc agccttacca gtaaaaaaga aacctatta aaaaaacacc actcgacacg | 35580 |
| gcaccagctc aatcagtcac agtgtaaaaa agggccaagt gcagagcgag tatatatagg | 35640 |
| actaaaaaat gacgtaacgg ttaaagtcca caaaaacac ccagaaaacc gcacgcgaac | 35700 |
| ctacgcccag aaacgaaagc caaaaaaccc acaacttcct caaatcgtca cttccgtttt | 35760 |
| cccacgttac gtaacttccc attttaagaa aactacaatt cccaacacat acaagttact | 35820 |
| ccgccctaaa acctacgtca cccgccccgt tcccacgccc cgcgccacgt cacaaactcc | 35880 |
| accccctcat tatcatattg gcttcaatcc aaaataaggt atattattga tgatg | 35935 |

<210> SEQ ID NO 5
<211> LENGTH: 1080
<212> TYPE: DNA
<213> ORGANISM: Homo sapiens

<400> SEQUENCE: 5

| | |
|---|---|
| atgaaggcca ctatcatcct ccttctgctt gcacaagttt cctgggctgg accgtttcaa | 60 |
| cagagaggct tatttgactt tatgctagaa gatgaggctt ctgggatagg cccagaagtt | 120 |

```
cctgatgacc gcgacttcga gccctcccta ggcccagtgt gcccctcccg ctgtcaatgc    180
catcttcgag tggtccagtg ttctgatttg ggtctggaca aagtgccaaa ggatcttccc    240
cctgacacaa ctctgctaga cctgcaaaac aacaaaataa ccgaaatcaa agatggagac    300
tttaagaacc tgaagaacct tcacgcattg attcttgtca acaataaaat tagcaaagtt    360
agtcctggag catttacacc tttggtgaag ttggaacgac tttatctgtc caagaatcag    420
ctgaaggaat tgccagaaaa aatgcccaaa actcttcagg agctgcgtgc ccatgagaat    480
gagatcacca aagtgcgaaa agttactttc aatggactga accagatgat tgtcatagaa    540
ctgggcacca atccgctgaa gagctcagga attgaaaatg ggctttccca gggaatgaag    600
aagctctcct acatccgcat tgctgatacc aatatcacca gcattcctca aggtcttcct    660
ccttcccttc cggaattaca tcttgatggc aacaaaatca gcagagttga tgcagctagc    720
ctgaaaggac tgaataattt ggctaagttg ggattgagtt tcaacagcat ctctgctgtt    780
gacaatggct ctctggccaa cacgcctcat ctgagggagc ttcacttgga caacaacaag    840
cttaccagag tacctggtgg gctggcagag cataagtaca tccaggttgt ctaccttcat    900
aacaacaata tctctgtagt tggatcaagt gacttctgcc cacctggaca caacaccaaa    960
aaggcttctt attcgggtgt gagtcttttc agcaacccgg tccagtactg ggagatacag   1020
ccatccacct tcagatgtgt ctacgtgcgc tctgccattc aactcggaaa ctataagtaa   1080

<210> SEQ ID NO 6
<211> LENGTH: 588
<212> TYPE: DNA
<213> ORGANISM: cytomegalovirus

<400> SEQUENCE: 6
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa atgtcgtaa caactccgcc ccattgacgc    540
aaatgggcgg taggcgtgta cggtgggagg tctatataag cagagctc              588

<210> SEQ ID NO 7
<211> LENGTH: 225
<212> TYPE: DNA
<213> ORGANISM: Bos taurus

<400> SEQUENCE: 7
ctgtgccttc tagttgccag ccatctgttg tttgcccctc cccgtgcctt ccttgaccc     60 tggaaggtgc cactcccact gtcctttcct aataaaatga ggaaattgca tcgcattgtc    120
tgagtaggtg tcattctatt ctgggggggtg ggtggggca ggacagcaag ggggaggatt    180
gggaagacaa tagcaggcat gctggggatg cggtgggctc tatgg                    225
```

-continued

```
<210> SEQ ID NO 8
<211> LENGTH: 5
<212> TYPE: PRT
<213> ORGANISM: Artificial
<220> FEATURE:
<223> OTHER INFORMATION: Synthetic

<400> SEQUENCE: 8

Gly Arg Gly Asp Ser
1               5

<210> SEQ ID NO 9
<211> LENGTH: 9
<212> TYPE: PRT
<213> ORGANISM: Artificial
<220> FEATURE:
<223> OTHER INFORMATION: Synthetic

<400> SEQUENCE: 9

Cys Asp Cys Arg Gly Asp Cys Phe Cys
1               5

<210> SEQ ID NO 10
<211> LENGTH: 13
<212> TYPE: PRT
<213> ORGANISM: Artificial
<220> FEATURE:
<223> OTHER INFORMATION: Synthetic

<400> SEQUENCE: 10

Gly Ser Cys Asp Cys Arg Gly Asp Cys Phe Cys Ser Gly
1               5                   10

<210> SEQ ID NO 11
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 11 atg cag cgg ctt ggg gcc acc ctg ctg tgc ctg ctg ctg gcg gcg gcg      48
Met Gln Arg Leu Gly Ala Thr Leu Leu Cys Leu Leu Leu Ala Ala Ala
1               5                   10                  15 gtc ccc acg gcc ccc gcg ccc gct ccg acg gcg acc tcg gct cca gtc      96
Val Pro Thr Ala Pro Ala Pro Ala Pro Thr Ala Thr Ser Ala Pro Val
                20                  25                  30 aag ccc ggc ccg gct ctc agc tac ccg cag gag gag gcc acc ctc aat     144
Lys Pro Gly Pro Ala Leu Ser Tyr Pro Gln Glu Glu Ala Thr Leu Asn
            35                  40                  45 gag atg ttc cgc gag gtt gag gaa ctg atg gag gac acg cag cac aaa     192
Glu Met Phe Arg Glu Val Glu Glu Leu Met Glu Asp Thr Gln His Lys
        50                  55                  60 ttg cgc agc gcg gtg gaa gag atg gag gca gaa gaa gct gct gct aaa     240
Leu Arg Ser Ala Val Glu Glu Met Glu Ala Glu Glu Ala Ala Ala Lys
65                  70                  75                  80 gca tca tca gaa gtg aac ctg gca aac tta cct ccc agc tat cac aat     288
Ala Ser Ser Glu Val Asn Leu Ala Asn Leu Pro Pro Ser Tyr His Asn
                85                  90                  95 gag acc aac aca gac acg aag gtt gga aat aat acc atc cat gtg cac     336
Glu Thr Asn Thr Asp Thr Lys Val Gly Asn Asn Thr Ile His Val His
            100                 105                 110
```

-continued

| | | |
|---|---|---|
| cga gaa att cac aag ata acc aac aac cag act gga caa atg gtc ttt<br>Arg Glu Ile His Lys Ile Thr Asn Asn Gln Thr Gly Gln Met Val Phe<br>115                        120                    125 | 384 | |
| tca gag aca gtt atc aca tct gtg gga gac gaa gaa ggc aga agg agc<br>Ser Glu Thr Val Ile Thr Ser Val Gly Asp Glu Glu Gly Arg Arg Ser<br>130                        135                    140 | 432 | |
| cac gag tgc atc atc gac gag gac tgt ggg ccc agc atg tac tgc cag<br>His Glu Cys Ile Ile Asp Glu Asp Cys Gly Pro Ser Met Tyr Cys Gln<br>145                        150                    155                    160 | 480 | |
| ttt gcc agc ttc cag tac acc tgc cag cca tgc cgg ggc cag agg atg<br>Phe Ala Ser Phe Gln Tyr Thr Cys Gln Pro Cys Arg Gly Gln Arg Met<br>                    165                    170                    175 | 528 | |
| ctc tgc acc cgg gac agt gag tgc tgt gga gac cag ctg tgt gtc tgg<br>Leu Cys Thr Arg Asp Ser Glu Cys Cys Gly Asp Gln Leu Cys Val Trp<br>                    180                    185                    190 | 576 | |
| ggt cac tgc acc aaa atg gcc acc agg ggc agc aat ggg acc atc tgt<br>Gly His Cys Thr Lys Met Ala Thr Arg Gly Ser Asn Gly Thr Ile Cys<br>195                        200                    205 | 624 | |
| gac aac cag agg gac tgc cag ccg ggg ctg tgc tgt gcc ttc cag aga<br>Asp Asn Gln Arg Asp Cys Gln Pro Gly Leu Cys Cys Ala Phe Gln Arg<br>210                        215                    220 | 672 | |
| ggc ctg ctg ttc cct gtg tgc aca ccc ctg ccc gtg gag ggc gag ctt<br>Gly Leu Leu Phe Pro Val Cys Thr Pro Leu Pro Val Glu Gly Glu Leu<br>225                        230                    235                    240 | 720 | |
| tgc cat gac ccc gcc agc cgg ctt ctg gac ctc atc acc tgg gag cta<br>Cys His Asp Pro Ala Ser Arg Leu Leu Asp Leu Ile Thr Trp Glu Leu<br>                    245                    250                    255 | 768 | |
| gag cct gat gga gcc ttg gac cga tgc cct tgt gcc agt ggc ctc ctc<br>Glu Pro Asp Gly Ala Leu Asp Arg Cys Pro Cys Ala Ser Gly Leu Leu<br>                    260                    265                    270 | 816 | |
| tgc cag ccc cac agc cac agc ctg gtg tat gtg tgc aag ccg acc ttc<br>Cys Gln Pro His Ser His Ser Leu Val Tyr Val Cys Lys Pro Thr Phe<br>275                        280                    285 | 864 | |
| gtg ggg agc cgt gac caa gat ggg gag atc ctg ctg ccc aga gag gtc<br>Val Gly Ser Arg Asp Gln Asp Gly Glu Ile Leu Leu Pro Arg Glu Val<br>290                        295                    300 | 912 | |
| ccc gat gag tat gaa gtt ggc agc ttc atg gag gag gtg cgc cag gag<br>Pro Asp Glu Tyr Glu Val Gly Ser Phe Met Glu Glu Val Arg Gln Glu<br>305                        310                    315                    320 | 960 | |
| ctg gag gac ctg gag agg agc ctg act gaa gag atg gcg ctg ggg gag<br>Leu Glu Asp Leu Glu Arg Ser Leu Thr Glu Glu Met Ala Leu Gly Glu<br>                    325                    330                    335 | 1008 | |
| cct gcg gct gcc gcc gct gca ctg ctg gga ggg gaa gag att tag<br>Pro Ala Ala Ala Ala Ala Leu Leu Gly Gly Glu Glu Ile<br>340                        345                    350 | 1053 | |

<210> SEQ ID NO 12
<211> LENGTH: 350
<212> TYPE: PRT
<213> ORGANISM: Homo sapiens

<400> SEQUENCE: 12

Met Gln Arg Leu Gly Ala Thr Leu Leu Cys Leu Leu Leu Ala Ala
1                 5                   10                   15

Val Pro Thr Ala Pro Ala Pro Ala Pro Thr Ala Thr Ser Ala Pro Val
                  20                   25                   30

Lys Pro Gly Pro Ala Leu Ser Tyr Pro Gln Glu Glu Ala Thr Leu Asn
                  35                   40                   45

Glu Met Phe Arg Glu Val Glu Glu Leu Met Glu Asp Thr Gln His Lys
50                        55                   60

```
Leu Arg Ser Ala Val Glu Met Glu Ala Glu Ala Ala Lys
 65              70                  75                  80

Ala Ser Ser Glu Val Asn Leu Ala Asn Leu Pro Pro Ser Tyr His Asn
             85                  90                  95

Glu Thr Asn Thr Asp Thr Lys Val Gly Asn Asn Thr Ile His Val His
            100                 105                 110

Arg Glu Ile His Lys Ile Thr Asn Asn Gln Thr Gly Gln Met Val Phe
            115                 120                 125

Ser Glu Thr Val Ile Thr Ser Val Gly Asp Glu Gly Arg Arg Ser
130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
            195                 200                 205

Asp Asn Gln Arg Asp Cys Gln Pro Gly Leu Cys Cys Ala Phe Gln Arg
210                 215                 220

Gly Leu Leu Phe Pro Val Cys Thr Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
            275                 280                 285

Val Gly Ser Arg Asp Gln Asp Gly Glu Ile Leu Leu Pro Arg Glu Val
            290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Leu Leu Gly Gly Glu Glu Ile
            340                 345                 350

<210> SEQ ID NO 13
<211> LENGTH: 720
<212> TYPE: DNA
<213> ORGANISM: Homo sapiens
<220> FEATURE:
<221> NAME/KEY: CDS
<222> LOCATION: (1)..(720)

<400> SEQUENCE: 13 atg cag cgg ctt ggg gcc acc ctg ctg tgc ctg ctg ctg gcg gcg gcg      48
Met Gln Arg Leu Gly Ala Thr Leu Leu Cys Leu Leu Leu Ala Ala Ala
1               5                   10                  15 gtc ccc acg gcc ccc gcg ccc gct ccg acg gcg acc tcg ggc aga agg      96
Val Pro Thr Ala Pro Ala Pro Ala Pro Thr Ala Thr Ser Gly Arg Arg
                20                  25                  30 agc cac gag tgc atc atc gac gag gac tgt ggg ccc agc atg tac tgc     144
Ser His Glu Cys Ile Ile Asp Glu Asp Cys Gly Pro Ser Met Tyr Cys
            35                  40                  45
```

| | | | | | | | | | | | | | | | | |
|---|---|---|---|---|---|---|---|---|---|---|---|---|---|---|---|---|
| cag | ttt | gcc | agc | ttc | cag | tac | acc | tgc | cag | cca | tgc | cgg | ggc | cag | agg | 192 |
| Gln | Phe | Ala | Ser | Phe | Gln | Tyr | Thr | Cys | Gln | Pro | Cys | Arg | Gly | Gln | Arg | |
| | 50 | | | | 55 | | | | | 60 | | | | | | |
| atg | ctc | tgc | acc | cgg | gac | agt | gag | tgc | tgt | gga | gac | cag | ctg | tgt | gtc | 240 |
| Met | Leu | Cys | Thr | Arg | Asp | Ser | Glu | Cys | Cys | Gly | Asp | Gln | Leu | Cys | Val | |
| 65 | | | | | 70 | | | | | 75 | | | | | 80 | |
| tgg | ggt | cac | tgc | acc | aaa | atg | gcc | acc | agg | ggc | agc | aat | ggg | acc | atc | 288 |
| Trp | Gly | His | Cys | Thr | Lys | Met | Ala | Thr | Arg | Gly | Ser | Asn | Gly | Thr | Ile | |
| | | | | 85 | | | | | 90 | | | | | 95 | | |
| tgt | gac | aac | cag | agg | gac | tgc | cag | ccg | ggg | ctg | tgc | tgt | gcc | ttc | cag | 336 |
| Cys | Asp | Asn | Gln | Arg | Asp | Cys | Gln | Pro | Gly | Leu | Cys | Cys | Ala | Phe | Gln | |
| | | | 100 | | | | | 105 | | | | | 110 | | | |
| aga | ggc | ctg | ctg | ttc | cct | gtg | tgc | aca | ccc | ctg | ccc | gtg | gag | ggc | gag | 384 |
| Arg | Gly | Leu | Leu | Phe | Pro | Val | Cys | Thr | Pro | Leu | Pro | Val | Glu | Gly | Glu | |
| | | | 115 | | | | | 120 | | | | | 125 | | | |
| ctt | tgc | cat | gac | ccc | gcc | agc | cgg | ctt | ctg | gac | ctc | atc | acc | tgg | gag | 432 |
| Leu | Cys | His | Asp | Pro | Ala | Ser | Arg | Leu | Leu | Asp | Leu | Ile | Thr | Trp | Glu | |
| | | 130 | | | | | 135 | | | | | 140 | | | | |
| cta | gag | cct | gat | gga | gcc | ttg | gac | cga | tgc | cct | tgt | gcc | agt | ggc | ctc | 480 |
| Leu | Glu | Pro | Asp | Gly | Ala | Leu | Asp | Arg | Cys | Pro | Cys | Ala | Ser | Gly | Leu | |
| 145 | | | | | 150 | | | | | 155 | | | | | 160 | |
| ctc | tgc | cag | ccc | cac | agc | cac | agc | ctg | gtg | tat | gtg | tgc | aag | ccg | acc | 528 |
| Leu | Cys | Gln | Pro | His | Ser | His | Ser | Leu | Val | Tyr | Val | Cys | Lys | Pro | Thr | |
| | | | | 165 | | | | | 170 | | | | | 175 | | |
| ttc | gtg | ggg | agc | cgt | gac | caa | gat | ggg | gag | atc | ctg | ctg | ccc | aga | gag | 576 |
| Phe | Val | Gly | Ser | Arg | Asp | Gln | Asp | Gly | Glu | Ile | Leu | Leu | Pro | Arg | Glu | |
| | | | 180 | | | | | 185 | | | | | 190 | | | |
| gtc | ccc | gat | gag | tat | gaa | gtt | ggc | agc | ttc | atg | gag | gag | gtg | cgc | cag | 624 |
| Val | Pro | Asp | Glu | Tyr | Glu | Val | Gly | Ser | Phe | Met | Glu | Glu | Val | Arg | Gln | |
| | | | 195 | | | | | 200 | | | | | 205 | | | |
| gag | ctg | gag | gac | ctg | gag | agg | agc | ctg | act | gaa | gag | atg | gcg | ctg | ggg | 672 |
| Glu | Leu | Glu | Asp | Leu | Glu | Arg | Ser | Leu | Thr | Glu | Glu | Met | Ala | Leu | Gly | |
| | | 210 | | | | | 215 | | | | | 220 | | | | |
| gag | cct | gcg | gct | gcc | gcc | gct | gca | ctg | ctg | gga | ggg | gaa | gag | att | tag | 720 |
| Glu | Pro | Ala | Ala | Ala | Ala | Ala | Leu | Leu | Gly | Gly | Glu | Glu | Ile | | | |
| 225 | | | | | 230 | | | | | 235 | | | | | | |

<210> SEQ ID NO 14
<211> LENGTH: 239
<212> TYPE: PRT
<213> ORGANISM: Homo sapiens

<400> SEQUENCE: 14

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Gly Arg Arg
                20                  25                  30

Ser His Glu Cys Ile Ile Asp Glu Asp Cys Gly Pro Ser Met Tyr Cys
            35                  40                  45

Gln Phe Ala Ser Phe Gln Tyr Thr Cys Gln Pro Cys Arg Gly Gln Arg
        50                  55                  60

Met Leu Cys Thr Arg Asp Ser Glu Cys Cys Gly Asp Gln Leu Cys Val
65                  70                  75                  80

Trp Gly His Cys Thr Lys Met Ala Thr Arg Gly Ser Asn Gly Thr Ile
                85                  90                  95

Cys Asp Asn Gln Arg Asp Cys Gln Pro Gly Leu Cys Cys Ala Phe Gln
            100                 105                 110

Arg Gly Leu Leu Phe Pro Val Cys Thr Pro Leu Pro Val Glu Gly Glu
        115                 120                 125

```
Leu Cys His Asp Pro Ala Ser Arg Leu Leu Asp Leu Ile Thr Trp Glu
    130             135             140

Leu Glu Pro Asp Gly Ala Leu Asp Arg Cys Pro Cys Ala Ser Gly Leu
145             150             155             160

Leu Cys Gln Pro His Ser His Ser Leu Val Tyr Val Cys Lys Pro Thr
                165             170             175

Phe Val Gly Ser Arg Asp Gln Asp Gly Glu Ile Leu Leu Pro Arg Glu
            180             185             190

Val Pro Asp Glu Tyr Glu Val Gly Ser Phe Met Glu Glu Val Arg Gln
        195             200             205

Glu Leu Glu Asp Leu Glu Arg Ser Leu Thr Glu Glu Met Ala Leu Gly
    210             215             220

Glu Pro Ala Ala Ala Ala Ala Leu Leu Gly Gly Glu Glu Ile
225             230             235
```

CONDITIONALLY REPLICATING ADENOVIRUS TO EXPRESS REIC GENE

CROSS-REFERENCE TO RELATED APPLICATIONS

This application is a National Stage application of PCT/JP2015/065004, filed May 26, 2015, which claims priority from Japanese application JP 2014-110672, filed May 28, 2014.

TECHNICAL FIELD

The present invention relates to a conditionally replicating adenovirus to highly express REIC (REIC/Dkk-3) protein.

BACKGROUND ART

Clinical trials on drugs for cancer with various conditionally replicating (genetically engineered to replicate specifically in a cancer cell) viruses have been previously reported (Non Patent Literature 1). Although treatments of cancer with these drugs have achieved certain results, the effect is limited in most cases, and development of more effective drugs is desired.

Representative examples of drugs for cancer with a conditionally replicating virus for which results of a clinical trial have been reported include Telomelysin (Non Patent Literature 2), which contains an adenovirus type 5 as a skeleton, and Talimogene laherparepvec (T-VEC, old name: Oncovex) (Non Patent Literature 3), which contains a herpes simplex virus type 1 as a skeleton.

In recent years, it has been considered important to allow drugs for cancer with a virus to have a function of activating anticancer immunity. From this viewpoint, although Telomelysin (Non Patent Literature 2) can induce cancer cell death through replication of the adenovirus at a location of administration, it does not encode a cytokine gene or the like which activates anticancer immunity, and thus a strong, systemic anticancer immunity-activating effect is not expected. This may limit the therapeutic effect of Telomelysin.

T-VEC is expected to provide cancer cell death and impart antigenicity to a cancer cell through replication of the herpes virus at a location of administration and to activate anticancer immunity through expression of the cytokine GM-CSF. Although the cytokine GM-CSF has an anticancer immunity-activating effect to induce a dendritic cell as a cancer antigen-presenting cell, to differentiate (Non Patent Literature 1), it has been also reported that the cytokine GM-CSF in a high dosage may induce an immunosuppressive cell to reduce the anticancer immune function to worsen disease condition (Non Patent Literature 4), which may limit the therapeutic effect of T-VEC.

Thus, development of more effective drugs for cancer is desired in light of the above problems of existing drugs for cancer with a conditionally replicating virus. As a conditionally replicating adenovirus to solve the above problems, conditionally replicating adenoviruses having various mutations have been reported (Patent Literatures 1 and 2 and Non Patent Literatures 5 to 10).

On the other hand, an REIC (REIC/Dkk-3) gene is known as a gene associated with immortalization of a cell, and it has been reported that expression of this gene is suppressed in cancer cells, and that the REIC gene is used for treatment of cancers (Patent Literature 3). The REIC has an anticancer immunity-activating effect and an effect of inducing cancer cell death through endoplasmic reticulum stress in gene expression. It is further reported that a partial fragment of the REIC gene has the same effect as the full length REIC (Patent Literature 4), and furthermore an adenovirus to express the REIC/Dkk-3 gene has been reported (Patent Literature 5 and Non Patent Literature 11).

CITATION LIST

Patent Literature

Patent Literature 1: JP Patent No. 4327844
Patent Literature 2: JP Patent Publication (Kohyo) No. 2008-531010
Patent Literature 3: International Publication No. WO2001/038528
Patent Literature 4: International Publication No. WO2012/002582
Patent Literature 5: International Publication No. WO2012/161352

Non Patent Literature

Non Patent Literature 1: R. V. Dave et al., Surgeon 2014, February 4
Non Patent Literature 2: John Nemunaitis et al., Molecular Therapy, Vol. 18, No. 2, 429-434, February 2010
Non Patent Literature 3: Neil N. Senzer et al., Journal of Clinical Oncology, Vol. 27, No. 34, Dec. 1, 2009, 5763-5771
Non Patent Literature 4: G. Parmiani et al., Annals of Oncology 18; 226-232, 2007
Non Patent Literature 5: Oh-Joon Kwon et al., Clin Cncer Res; 16(24) Dec. 15, 2010
Non Patent Literature 6: Eunhee Kim et al., Human Gene Therapy 14:1415-1428 (Oct. 10, 2003), 1415-1427
Non Patent Literature 7: Candelaria Gomez-Manzano et al., Onvogene (2004)23, 1821-1828
Non Patent Literature 8: Jaesung Kim et al., Cancer Gene Therapy (2002)9, 725-736
Non Patent Literature 9: I-K Choi et al., Gene Therapy (2010) 17, 190-201
Non Patent Literature 10: Hao Wu et al., J Gene Med 2011; 13: 658-669
Non Patent Literature 11: Watanabe M et al., Oncology Letters 7: 595-601, 2004

SUMMARY OF INVENTION

Technical Problem

An object of the present invention is to provide a conditionally replicating adenovirus having a strong anticancer effect.

Solution to Problem

The present inventors effectively combined previously reported techniques relating to conditionally replicating adenoviruses (Patent Literatures 1 and 2 and Non Patent Literatures 5 to 10) to produce a unique conditionally replicating adenovirus. In addition, the adenovirus was newly allowed to encode the REIC gene which expresses REIC protein, which has a unique anticancer immunity-activating effect (Non Patent Literature 11). By virtue of this, the present inventors succeeded in development of an anticancer virus formulation of high inventiveness having uniqueness and novelty in combination and being expected to be far superior to existing drugs for cancer with a conditionally replicating virus, and thus completed the present invention.

Specifically, the present invention is as follows:

[1] A conditionally replicating adenovirus to replicate specifically in a cancer cell and express REIC protein or REIC C domain protein, wherein the conditionally replicating adenovirus is obtained by inserting full-length REIC DNA or REIC C domain DNA into a conditionally replicating adenovirus comprising an ITR (inverted terminal repeat) sequence of an adenovirus type 5 genome and insertion of an HRE sequence, an hTERT promoter, a decorin-encoding DNA, and a DNA encoding a peptide comprising an RGD sequence.

[2] The conditionally replicating adenovirus according to [1], wherein a DNA construct consisting of a promoter sequence, the decorin-encoding DNA, and a poly A addition sequence is inserted into an E3 region of the adenovirus type 5.

[3] The conditionally replicating adenovirus according to [1] or [2], wherein
(i) the hTERT promoter is an hTERT promoter modified through addition of a c-Myc binding site and an Sp1 binding site;
(ii) six HRE sequences each consisting of a nucleotide sequence as set forth in SEQ ID NO: 3 are inserted into upstream of the hTERT promoter;
(iii) an Rb binding region (Retinoblastoma gene binding region), being a part of an E1A region, in the adenovirus type 5 genome sequence as set forth in as SEQ ID NO: 4 is deleted;
(iv) nucleotides of a portion encoding E1B-19 kDa, being a part of an E1B region, in the adenovirus type 5 genome sequence as set forth in as SEQ ID NO: 4 are deleted;
(v) an E3 region is partially deleted;
(vi) a DNA construct consisting of a promoter sequence, the decorin-encoding DNA, and a poly A addition sequence is inserted into the E3 region;
(vii) the DNA encoding a peptide comprising an RGD sequence is inserted into the E3 region; and
(viii) a DNA construct consisting of a CMV promoter sequence, a DNA encoding REIC DNA or REIC C domain DNA, and a poly A addition sequence is inserted into an E1 region.

[4] The conditionally replicating adenovirus according to [3], wherein
(iii) 24 nucleotides at positions 923 to 946 as the Rb binding region (Retinoblastoma gene binding region), being a part of the E1A region, in the adenovirus type 5 genome sequence as set forth in SEQ ID NO: 4 are deleted;
(iv) nucleotides at positions 1722 to 1986 as the portion encoding E1B-19 kDa, being a part of the E1B region, in the adenovirus type 5 genome sequence as set forth in as SEQ ID NO: 4 are deleted; and
(v) nucleotides at positions 28592 to 30479, being a part of the E3 region, in the adenovirus type 5 genome sequence as set forth in as SEQ ID NO: 4 are deleted.

[5] The conditionally replicating adenovirus according to any one of [1] to [4], wherein REIC is full length REIC.

[6] The conditionally replicating adenovirus according to any one of [1] to [4], wherein REIC is REIC C domain.

[7] A cancer therapeutic agent comprising the conditionally replicating adenovirus according to any one of [1] to [6] as an active ingredient.

[8] The cancer therapeutic agent according to [7], wherein the conditionally replicating adenovirus replicates specifically in a cancer cell and expresses REIC protein, and the REIC protein expressed induces cancer cell death through endoplasmic reticulum stress, and the REIC protein further induces a systemic anticancer immune activity.

The present specification encompasses the contents described in the specification and/or drawings of JP Patent Application No. 2014-110672, on which the priority of the present application is based.

Advantageous Effects of Invention

The conditionally replicating adenovirus according to the present invention results from improvement of a conventional conditionally replicating adenovirus, and has a stronger anticancer effect than conventional conditionally replicating adenoviruses. In addition, the conditionally replicating adenovirus into which REIC DNA has been inserted, in addition to an anticancer effect of the conditionally replicating adenovirus itself, an anticancer immunity-activating effect and an effect of inducing cancer cell death through endoplasmic reticulum stress in gene expression each provided by REIC in combination, and these effects cooperate to exert a synergistic, strong therapeutic effect against cancer.

DESCRIPTION OF EMBODIMENTS

Figure 1:
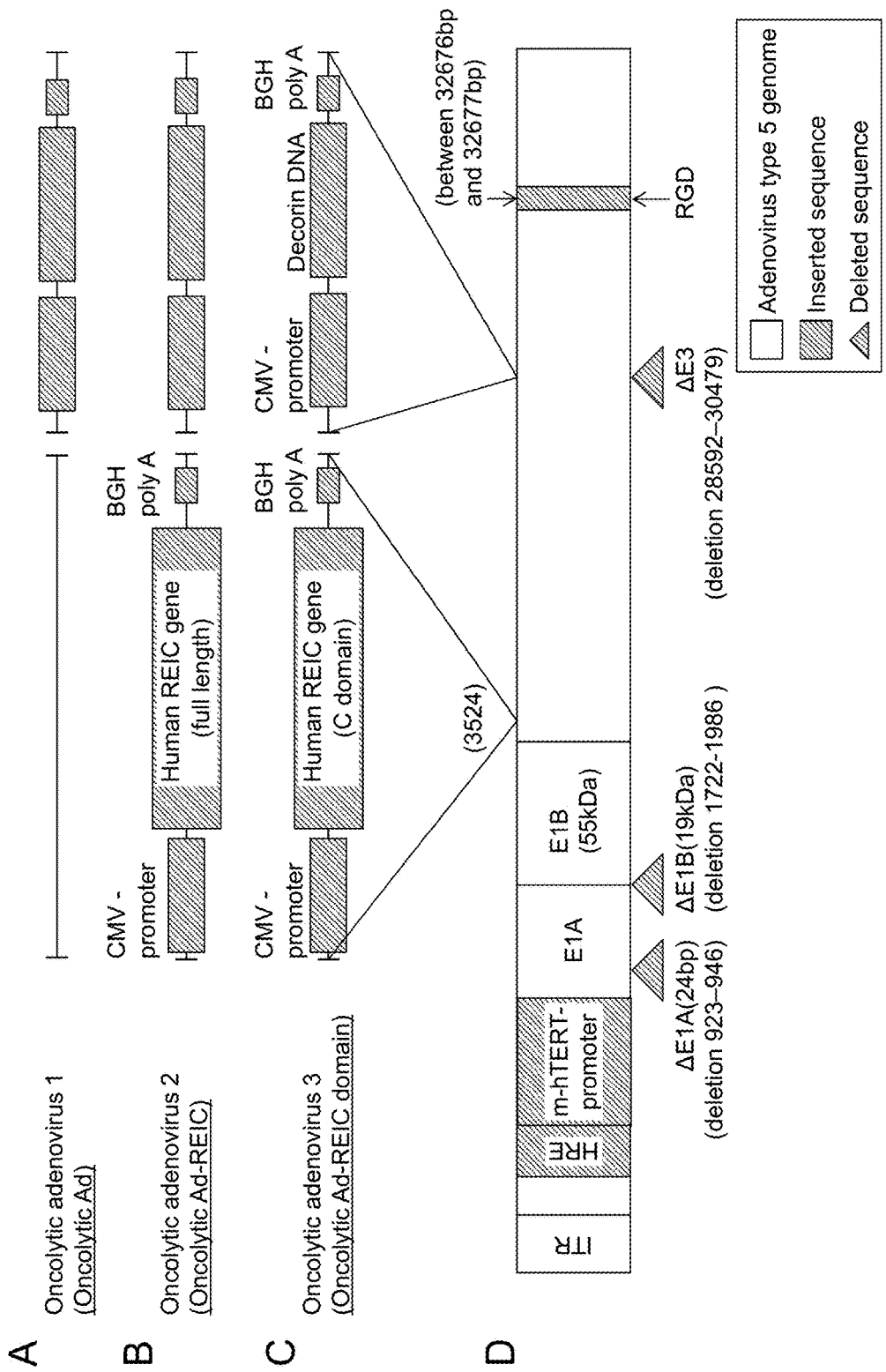
FIG. 1 illustrates the structures of oncolytic adenoviruses.

Now, the present invention will be described in detail.

The present invention is a conditionally replicating adenovirus which comprises REIC (REIC/Dkk-3) DNA and can be used for expression of REIC protein.

A conditionally replicating adenovirus, which refers to an adenovirus genetically engineered to replicate only in cancer cells, does not act on normal cells, and replicates only in cancer cells and lyses a cancer cell to effectively kill it. Conditionally replicating adenoviruses are also called oncolytic adenoviruses or tumorlytic adenoviruses. The conditionally replicating adenovirus according to the present invention can be used with a foreign gene inserted thereinto, and thus can be regarded as a conditionally replicating adenovirus vector.

The conditionally replicating adenovirus according to the present invention, into which full-length REIC DNA or an REIC DNA fragment has been introduced, has, in addition to a cancer cell-killing effect of the conditionally replicating adenovirus itself, effects on cancer cells provided by REIC such as an anticancer immunity-activating effect and an effect of inducing cancer cell death through endoplasmic reticulum stress in gene expression, and thus can exert a synergistic cancer cell-killing effect.

In the present invention a conditionally replicating adenovirus is called an oncolytic adenovirus (oncolytic Ad), a conditionally replicating adenovirus which comprises full-length REIC DNA and can express full-length REIC is called an oncolytic Ad-REIC, and a conditionally replicating adenovirus which comprises REIC C domain DNA and can express an REIC C domain is called an oncolytic Ad-REIC domain.

Each of the conditionally replicating adenoviruses used in the present invention has a skeleton of an adenovirus type 5 whose replication is limited by a human telomerase reverse transcriptase (hTERT) promoter. The conditionally replicating adenovirus according to the present invention comprises an ITR (inverted terminal repeat) of an adenovirus type 5 and further comprises a decorin-encoding DNA, where decorin is a protein which suppresses the formation and growth of a tumor, and contains other modifications (insertion and deletion of specific sequences). The decorin DNA is expressed by a CMV promoter. The genome sequence of the adenovirus type 5 is set forth in Virology, 186 (1), 1992, pp. 280-285, and registered as GenBank Accession No. M73260. The genome sequence of the adenovirus type 5 is set forth in SEQ ID NO: 4. The genome of the adenovirus contains an ITR (inverted terminal repeat) at each end, and contains an E1A region, E1B region, E2 region, E3 region, and E4 region in the order from the 5' side, as initially transcribed regions.

Features of the conditionally replicating adenovirus according to the present invention are as follows.

(1) An ITR (inverted terminal repeat) of the adenovirus type 5 is comprised. The ITR consists of 100 to 200 nucleotides and is an element essential for replication and packaging of the adenovirus DNA.

Figure 2:
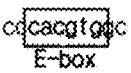
FIG. 2 shows a sequence of an m-hTERT promoter.

(2) A human telomerase reverse transcriptase (hTERT) promoter is comprised. The hTERT promoter is comprised in the upstream of the E1 region of the adenovirus type 5 genome, and is linked, for example, to the immediate upstream of the E1 region. Preferably, the hTERT promoter has been modified. A modified hTERT promoter is called an m-hTERT promoter. A modified hTERT promoter comprises one or more c-Myc binding sites (cacgtg, cacgcg, or catgcg) and/or one or more Sp1 binding sites (gggcgg, ccgccc, ctccgcctc, cccagcccc, gggcgg, ggggcgg, or cccccgcccc) (SEQ ID NO: 1). A wild-type hTERT promoter comprises two c-Myc binding sites and five Sp1 binding sites. The hTERT promoter of the conditionally replicating adenovirus according to the present invention comprises, for example, three c-Myc binding sites and 10 Sp1 binding sites in total with further addition of one c-Myc binding site and five Sp1 binding sites. The c-Myc binding site and Sp1 binding site may be comprised at the 3' end or 5' end of the hTERT promoter, or may be comprised in the interior of the hTERT promoter sequence. One exemplary sequence of modified hTERT promoters is set forth in FIG. 2 and SEQ ID NO: 2. In FIG. 1, each "E-box" indicates a c-Myc binding sequence. To produce an m-hTERT promoter in which an hTERT promoter further comprises one c-Myc binding site and five Sp1 binding sites (SEQ ID NO: 2), for example, a wile-type hTERT promoter containing two c-Myc binding sites and five Sp1 binding sites is suitably allowed to bind to an hTERT promoter containing one c-Myc binding site and five Sp1 binding sites. To achieve this, it is suitable that a pGL2-hTERT vector comprising one c-Myc binding site and five Sp1 binding sites is first cut with EcoRI and HindIII, and the resultant is then inserted into pSEAP-TERT treated with the same restriction enzymes to produce pSEAP-mTERT. The modified hTERT promoter is described in JP Patent No. 4327844 and EUNHEE KIM et al., Human Gene Therapy 14: 1415-1428 (Oct. 10, 2003).

(3) A hypoxia responsive element (HRE) is comprised. The HRE, which is a DNA element having a gene to be activated by hypoxia and responds to hypoxia, comprises ACGTG as a consensus sequence. Conditionally replicating adenoviruses used in the present invention comprise a sequence consisting of 5 to 40 nucleotides comprising the consensus sequence. Oxygen concentration is approximately 2 to 9% in a normal tissue. In contrast, oxygen concentration is approximately 1.3% in a cancer cell, which indicates hypoxia. As a result, replication of a conditionally replicating adenovirus comprising an HRE is accelerated in a cancer cell. Examples of HRE sequences include a sequence comprising the consensus sequence in a human vascular endothelial growth factor (hVEGF) gene (GenBank Accession No. M63971), specifically, the nucleotide sequence from the 1379th nucleotide to the 1412th nucleotide in the hVEGF gene (SEQ ID NO: 3). A plurality of HREs linked may be used, and for example, 3 to 12 HREs linked may be used, or six HREs linked (HRE×6) or 12 HREs linked (HRE×12) may be used (Oh-Joon Kwon et al., Clin Cancer Res; 16(24) Dec. 15, 2010, pp. 60716082). Preferably, six HREs linked (HRE×6) is used. The HRE is suitably linked to the upstream of the hTERT promoter, for example, to the immediate upstream of the hTERT promoter.

(4) An E1A region is partially deleted. The E1A region is a region at positions 342 to 1545 in the adenovirus type 5 genome (SEQ ID NO: 4), and E1A protein binds to an RB (Retinoblastoma) gene product. The E1A region is a region essential for replication of adenoviruses, and the conditionally replicating adenovirus according to the present invention contains deletion of an Rb binding region (Retinoblastoma gene binding region) in the E1A and possesses replication capability itself. The partial deletion of the E1A region in the conditionally replicating adenovirus according to the present invention is also described as "comprising a modified and active E1A gene". Here, the modified and active E1A gene contains a mutation causing substitution of Glu residue at position 45 with Gly and a mutation causing total substitution of the amino acid sequence at positions 121 to 127 with Gly in a nucleotide sequence encoding the Rb (retinoblastoma protein) binding site. In a tumor cell, not only p53 protein is mutated, but also Rb is mutated or Rb-related signaling mechanism is significantly damaged. Thus, an adenovirus with the binding ability to Rb deleted is suppressed from replication due to the activity of Rb in a normal cell, and in contrast, actively replicates in a tumor cell, in which the function of Rb is suppressed, and thus a cancer cell can be selectively killed. Accordingly, the recombinant adenovirus according to the present invention, which comprises the above-described mutation in the Rb binding site, has highly enhanced specificity to cancer cells. For a mutation in the Rb binding site, for example, 24 nucleotides at positions 923 to 946, being a part of the E1A region, as the Rb binding region (Retinoblastoma gene binding region) in the adenovirus type 5 genome sequence as set forth in SEQ ID NO: 4 may be deleted (ΔE1A (24 bp)) (Candelaria Gomez-Manzano et al., Oncogene (2004) 23, pp. 1821-1828).

(5) An E1B region is partially deleted. The E1B region is a region at positions 1714 to 3509 in the adenovirus type 5 genome (SEQ ID NO: 4), and E1B-55 kDa protein, a gene product of the E1B region, is involved in replication of a virus through binding to p53 protein. The partial deletion of the E1B region is also described as "containing an inactivated portion in the E1B region", and the conditionally replicating adenovirus according to the present invention contains an inactivated E1B 19 kDa gene, E1B 55 kDa gene, or E1B 19 kDa/E1B 55 kDa gene, and preferably contains inactivated E1B 19 kDa and E1B 55 kDa genes. In the present specification, "inactivation" used in relation to a gene means that a gene is not transcribed and/or decoded normally, and the protein encoded by the gene lacks its normal function. For example, an inactivated E1B 19 kDa gene is a gene in which a mutation (substitution, addition, partial deletion, or total deletion) has been generated and cannot produce active E1B 19 kDa protein. In the case that the E1B 19 kDa gene is deleted, the apoptotic capability of a cell can be enhanced, and if the E1B 55 kDa gene is deleted, specificity to tumor cells is provided (KR Patent Application No. 100528727). For example, nucleotides at positions 1722 to 1986, being a part of the E1B region, in the adenovirus type 5 genome sequence as set forth in SEQ ID NO: 4 are suitably deleted. Deletion of this nucleotide sequence leads to deletion of a portion encoding E1B-19 kDa of 19 kDa, as a trans-splicing product of E1B protein of 55 kDa, and thus this deletion is called ΔE1B (19 kDa) (Jaesung Kim et al., Cancer Gene Therapy (2002) 9, pp. 725-736). Alternatively, a stop codon may be introduced so that only the E1B (19 kDa) is not expressed in the E1B region.

(6) An E3 region is deleted. It is only required that a DNA encoding E3 protein be totally or partially deleted. The E3 region is a region at positions 27858 to 30839 in the adenovirus type 5 genome (SEQ ID NO: 4). The E3 region is not required for replication of adenoviruses and a foreign gene can be inserted into the E3 region. In this case, it is suitable that the E3 region is partially deleted and a foreign gene is inserted into the portion. For example, nucleotides at positions 28592 to 30479, being a part of the E3 region, in the adenovirus type 5 genome sequence as set forth in SEQ ID NO: 4 are suitably deleted (4E3). Into this portion, a decorin-encoding DNA to be described later can be inserted, for example.

(7) A decorin (DCN)-encoding DNA, where decorin is a protein which suppresses the formation and growth of a tumor, is inserted. Decorin is a protein belonging to SLRPs (small leucine-rich proteoglycan) and contains 10 to 12 leucine-rich repeats, and the core site is arch-shaped and binds to several types of growth factors present in the extracellular matrix or a decorin receptor. Decorin acts as a natural antagonist for the formation and growth of a tumor through suppression of the activity of a tumor growth factor (TGF-β) to prevent fibrillation of collagen and association with the matrix assembly to suppress the growth of a tumor cell. Introduction of decorin into a conditionally replicating adenovirus facilitates introduction of the conditionally replicating adenovirus into a cancer cell to enhance the tumor cell-killing activity. In the conditionally replicating adenovirus according to the present invention, a promoter is linked to the upstream of the decorin-encoding DNA, and a poly A addition sequence (polyadenylated sequence, polyA) is linked to the downstream of the decorin-encoding DNA. The promoter is a promoter which operates preferably in an animal cell, more preferably in a mammalian cell and can regulate transcription of the decorin gene, and examples thereof include, but are not limited to, promoters derived from mammalian viruses and promoters derived from mammalian cell genomes, such as a U6 promoter, an H1 promoter, a CMV (Cytomegalovirus) promoter, an adenovirus late promoter, a vaccinia virus 7.5K promoter, an SV40 promoter, a tk promoter of an HSV, an RSV promoter, an EF1α promoter, a metallothionein promoter, a β-actin promoter, a promoter of the human IL-2 gene, a promoter of the human IFN gene, a promoter of the human IL-4 gene, a promoter of the human lymphotoxin gene, a promoter of the human GM-CSF gene, inducible promoters, cancer cell-specific promoters (e.g., a TERT promoter, a PSA promoter, a PSMA promoter, a CEA promoter, an E2F promoter and an AFP promoter), and tissue-specific promoters (e.g., an albumin promoter). Preferably, a CMV promoter or a cancer cell-specific promoter is used. In the case that a cancer cell-specific promoter is used, it is preferred to use a TERT promoter or an E2F promoter. For the TERT (telomere reverse transcriptase) promoter, a wild-type hTERT (human telomere reverse transcriptase) promoter or an m-hTERT promoter described in (2) may be used. The origin of the poly A addition sequence (polyadenylated sequence, polyA) is not limited, and examples thereof include a poly A addition sequence derived from a growth hormone gene such as a poly A addition sequence derived from the bovine growth hormone gene (BGH polyA) and a poly A addition sequence derived from the human growth hormone gene, a poly A addition sequence derived from an SV40 virus, and a poly A addition sequence derived from the human or rabbit β-globin gene. The poly A addition sequence comprised in a DNA construct increases the transcription efficiency.

An adenovirus containing the decorin-encoding DNA is described in JP Patent Publication (Kokai) No. 2008-531010 and I-K Choi et al., Gene Therapy (2010)17, 190-201. The nucleotide sequence of the decorin-encoding DNA (GenBank Accession No. NM_001920.3) is set forth in SEQ ID NO: 5. The nucleotide sequence of the CMV promoter (GenBank Accession No. X17403) and the nucleotide sequence of the BGH poly A addition sequence (GenBank Accession No. M57764) are set forth in SEQ ID NO: 6 and SEQ ID NO: 7, respectively.

A DNA construct comprising the decorin-encoding DNA and consisting of the promoter sequence, the decorin-encoding DNA, and the poly A addition sequence is suitably inserted into the E1A region, the E1B region, or the E3 region, and is preferably inserted into the E3 region. In the adenovirus vector according to the present invention, the E1A region, E1B region, and E3 region of the adenovirus type 5 genome are partially deleted, as described below. The DNA construct in which the CMV promoter, the decorin-encoding DNA, and the poly A addition sequence are linked in the order presented is suitably inserted into the deleted portion. For example, the DNA construct can be inserted into the adenovirus type 5 genome concomitantly with partial deletion of the E1A region, E1B region, and E3 region through homologous recombination. For example, the DNA construct is suitably inserted into the deleted portion of the 28592nd to 30479th nucleotides in the adenovirus type 5 genome sequence as set forth in SEQ ID NO: 4, described in the above (6).

(8) A DNA encoding a peptide comprising an RGD (Arg-Gly-Asp) sequence is inserted. Examples of peptides comprising an RGD sequence include RGD-comprising peptides consisting of 4 (e.g., GRGDS (SEQ ID NO: 8)) to 15 amino acids, such as peptides represented by CDCRGDCFC (SEQ ID NO: 9) and GSCDCRGDCFCSG (SEQ ID NO: 10). The DNA encoding a peptide comprising an RGD sequence is inserted, for example, into the E3 region, and is suitably inserted, specifically, between the 32676th nucleotide and the 32677th nucleotide in the E3 region in the adenovirus type 5 genome. The DNA encoding a peptide comprising an RGD sequence comprised in a conditionally replicating adenovirus facilitates introduction of the conditionally replicating adenovirus into a cancer cell. An adenovirus comprising an RGD sequence is described, for example, in Hao Wu et al., J Gene Med 2011; 13: 658-669.

The conditionally replicating adenovirus, with the above features (1) to (8), according to the present invention comprises the ITR (inverted terminal repeat) sequence of the adenovirus type 5 genome and has a structure in which the HRE sequence, the hTERT promoter, the decorin-encoding DNA, and the DNA encoding a peptide comprising an RGD sequence are inserted.

FIG. 1A illustrates an example of the structure of the conditionally replicating adenovirus according to the present invention. FIG. 1D illustrates mutations from a wild-type adenovirus type 5 in the conditionally replicating adenovirus according to the present invention, and insertion positions of the decorin DNA and the REIC DNA are also illustrated therein. FIG. 1B and FIG. 1C each illustrate the structure of a conditionally replicating adenovirus into which the REIC DNA is inserted. In the structure illustrated in FIG. 1A, referring to the structure of the conditionally replicating adenovirus illustrated in FIG. 1D, a DNA construct in which the CMV promoter, the decorin-encoding DNA, and the poly A addition sequence are linked in the order presented is inserted into the E3 region. In the conditionally replicating adenovirus the structure of which is illustrated in FIG. 1A, the E1A region of the adenovirus type 5 genome is partially deleted, the E1B region is partially deleted, and further the E3 region is partially deleted, and the HRE sequence and a modified hTERT promoter are comprised in the upstream of the E1A region, and the DNA encoding a peptide comprising an RGD sequence is comprised in the downstream of the E3 region, and further the construct consisting of the promoter, the decorin-encoding DNA, and the polyA sequence is comprised in the E3 region.

For example, the conditionally replicating adenovirus according to the present invention illustrated in FIG. 1A has the following structural features:
(i) the hTERT promoter is an hTERT promoter modified through addition of a c-Myc binding site and an Sp1 binding site;
(ii) six HRE sequences each consisting of a nucleotide sequence as set forth in SEQ ID NO: 3 are inserted into upstream of the hTERT promoter;
(iii) an Rb binding region (Retinoblastoma gene binding region), being a part of an E1A region, in the adenovirus type 5 genome sequence as set forth in as SEQ ID NO: 4 is deleted; for example, 24 nucleotides at positions 923 to 946 as the Rb binding region (Retinoblastoma gene binding region) in the adenovirus type 5 genome sequence as set forth in SEQ ID NO: 4 are deleted;
(iv) nucleotides of a portion encoding E1B-19 kDa, being a part of an E1B region, in the adenovirus type 5 genome sequence as set forth in as SEQ ID NO: 4 are deleted; for example, nucleotides at positions 1722 to 1986 as the portion encoding E1B-19 kDa in the adenovirus type 5 genome sequence as set forth in as SEQ ID NO: 4 are deleted;
(v) an E3 region is partially deleted; for example, nucleotides at positions 28592 to 30479 in the adenovirus type 5 genome sequence as set forth in as SEQ ID NO: 4 are deleted;
(vi) a DNA construct consisting of a promoter sequence, the decorin-encoding DNA, and a poly A addition sequence is inserted into the E3 region; and
(vii) the DNA encoding a peptide comprising an RGD sequence is inserted into the E3 region.

A multi-cloning site (insertion site) for insertion of a foreign gene may be contained in the E1A region, E1B region, or E3 region. A foreign gene such as REIC DNA to be described later can be inserted into the multi-cloning site.

The above elements need to be operably linked. Here, "operably linked" means that elements are linked so that each element exerts the function and expression of a gene to be expressed is enhanced.

For example, the conditionally replicating adenovirus according to the present invention has a structure represented by ITR-4E1A-4E1B-promoter-decorin DNA-poly A addition sequence-RGD sequence-ITR, and the construct consisting of "promoter-decorin DNA-poly A addition sequence" is inserted into a deleted portion of the E3 region. The structure (gene map) of such a conditionally replicating adenovirus is illustrated in FIG. 1.

An oncolytic Ad-REIC or an oncolytic Ad-REIC domain can be produced by inserting full-length REIC DNA or REIC C domain DNA into the above conditionally replicating adenovirus (oncolytic Ad).

The nucleotide sequence of the REIC DNA is set forth in SEQ ID NO: 11. The amino acid sequence of REIC protein encoded by the REIC DNA is set forth in SEQ ID NO: 12. In the present invention, REIC is occasionally referred to as REIC/Dkk-3.

The nucleotide sequence of the REIC C domain DNA is set forth in SEQ ID NO: 13, and the amino acid sequence of REIC C domain protein encoded by the domain is set forth in SEQ ID NO: 14.

The REIC DNA or REIC C domain DNA comprised in the conditionally replicating adenovirus according to the present invention is a DNA encoding a protein having an anticancer immunity-activating effect and an effect of inducing cancer cell death through endoplasmic reticulum stress in gene expression, among DNAs to hybridize with a DNA containing a nucleotide sequence complementary to a nucleotide sequence as set forth in SEQ ID NO: 11 or 13 under stringent conditions, DNAs having sequence identity of at least 85% or more, preferably 90% or more, more preferably 95% or more, particularly preferably 97% or more to a nucleotide sequence as set forth in SEQ ID NO: 11 or 13 as calculated by using a BLAST (Basic Local Alignment Search Tool at the National Center for Biological Information) or the like (e.g., with default parameters, i.e., initially set parameters), DNAs encoding a protein consisting of an amino acid sequence obtained by providing the amino acid sequence of a protein encoded by the DNA with substitution, deletion, and/or addition of one or several (1 to 10, preferably 1 to 5, more preferably 1 or 2) amino acids, and other DNAs. Here, "stringent conditions" refer to conditions of around "1×SSC, 0.1% SDS, 37° C.", more stringent conditions refer to conditions of around "0.5×SSC, 0.1% SDS, 42° C.", and even more stringent conditions refer to conditions of around "0.2×SSC, 0.1% SDS, 65° C.". It is expected that the more stringent hybridization conditions are as mentioned, the higher homology to a probe sequence a DNA isolated has. It is to be noted that the combinations of SSC, SDS, and temperature are just examples, and stringency required can be achieved by appropriately combining probe concentration, probe length, reaction duration for hybridization, etc. Those skilled in the art could appropriately determine "stringent conditions" for hybridization of a DNA with high sequence identity. Further, the REIC DNA comprised in the DNA construct in the present invention is a DNA encoding a protein as set forth in SEQ ID NO: 2.

The REIC DNA or REIC C domain DNA can be obtained from a human cell, a human tissue, or the like on the basis of sequence information of SEQ ID NOs: 11 to 14.

A CMV (cytomegalovirus) promoter is linked to the upstream of the full length REIC DNA or REIC C domain DNA, and to the downstream thereof a poly A addition sequence (polyadenylated sequence, polyA) is linked. The origin of the poly A addition sequence (polyadenylated sequence, polyA) is not limited, and examples thereof include a poly A addition sequence derived from a growth hormone gene such as a poly A addition sequence derived from the bovine growth hormone gene (BGH polyA) and a poly A addition sequence derived from the human growth hormone gene, a poly A addition sequence derived from an SV40 virus, and a poly A addition sequence derived from the human or rabbit β-globin gene. The poly A addition sequence comprised in a DNA construct increases the transcription efficiency. The nucleotide sequence of the CMV promoter (GenBank Accession No. X17403) and the nucleotide sequence of the BGH poly A addition sequence are set forth in SEQ ID NO: 6 and SEQ ID NO: 7, respectively.

A DNA construct comprising the DNA encoding the REIC DNA or REIC C domain DNA and consisting of the CMV promoter sequence, the DNA encoding the REIC DNA or REIC C domain DNA, and the poly A addition sequence is suitably inserted into the E1A region, E1B region, or E3 region, and is preferably inserted into the E1 region (E1A or E1B region). For example, the DNA construct can be inserted into the E1A region, E1B region, or E3 region of the adenovirus type 5 genome through homologous recombination.

For example, the DNA construct is suitably inserted into the E1 region of the above conditionally replicating adenovirus. In homologous recombination, only the DNA construct comprising the DNA encoding the REIC DNA or REIC C domain DNA and consisting of the CMV promoter sequence, the DNA encoding the REIC DNA or REIC C domain DNA, and the poly A addition sequence may be inserted, or a construct containing the E1 region which is obtained by inserting a DNA construct comprising the REIC DNA or REIC C domain DNA into the E1 region and partially deleting each of the E1A region and the E1B may be inserted through homologous recombination. This homologous recombination enables insertion of the DNA construct comprising the REIC DNA or REIC C domain DNA into the adenovirus type 5 concomitant with partial deletion of the E1A region and E1B region (4E1A (24 bp) and ΔE1B (19 kDa)) in the adenovirus type 5.

For example, the DNA construct is suitably inserted, specifically, between the nucleotide at position 342 and the nucleotide at position 3522 in the adenovirus type 5 genome sequence as set forth in SEQ ID NO: 4 through homologous recombination. For example, the DNA construct comprising the DNA encoding the REIC DNA or REIC C domain DNA and consisting of the CMV promoter sequence, the DNA encoding the REIC DNA or REIC C domain DNA, and the poly A addition sequence is suitably inserted into the E1 region through homologous recombination with pE1sp1B-HmT-Rd19/CMV-REIC-polA ((left homology portion: 22-341) (right homology portion: 3523-5790)) as an E1 shuttle vector. With use of this shuttle vector, the following DNA construct is inserted between position 342 and position 3522 in the adenovirus type 5 genome sequence.

A construct in which the DNA construct consisting of the CMV promoter sequence, the DNA encoding the REIC DNA or REIC C domain DNA, and the poly A addition sequence is inserted into the E1 region, and the Rb binding site in the E1A region is deleted, and the portion encoding the E1B-19 kDa in the E1B region is deleted.

Thus, the DNA construct consisting of the CMV promoter sequence, the DNA encoding the REIC DNA or REIC C domain DNA, and the poly A addition sequence can be inserted into the adenovirus type 5 concomitantly with partial deletion of the E1A region and E1B region (ΔE1A (24 bp) and ΔE1B (19 kDa)) in the adenovirus type 5.

Alternatively, the DNA construct consisting of the CMV promoter sequence, the DNA encoding the REIC DNA or REIC C domain DNA, and the poly A addition sequence may be inserted, for example, between position 3524 and position 3525 or between position 3523 and position 3524 in the adenovirus type 5 genome sequence.

The structure of the conditionally replicating adenovirus into which the DNA encoding the REIC DNA or REIC C domain DNA is illustrated in FIGS. 1B (oncolytic Ad-REIC) and 1C (oncolytic AD-REIC domain). In the structures illustrated in FIGS. 1B and 1C, the DNA construct consisting of the CMV promoter sequence, the DNA encoding the REIC DNA or REIC C domain DNA, and the poly A addition sequence is inserted into position 3524 in the E1 region in the conditionally replicating adenovirus (oncolytic Ad) the structure of which is illustrated in FIG. 1A.

The above elements need to be operably linked. Here, "operably linked" means that elements are linked so that each element exerts the function and expression of a gene to be expressed is enhanced.

The conditionally replicating adenovirus (oncolytic Ad), conditionally replicating adenovirus comprising the full length REIC DNA (oncolytic Ad-REIC), or conditionally replicating adenovirus comprising the REIC C domain DNA (Ad-REIC C domain) according to the present invention can be produced in accordance with the above description and the descriptions of the cited references.

The conditionally replicating adenovirus (oncolytic Ad) according to the present invention administered to a subject of a human or another mammal is delivered to a cancer cell in the subject and replicates in the cancer cell to kill the cancer cell.

Each of the conditionally replicating adenovirus comprising the full length REIC DNA (oncolytic Ad-REIC) and conditionally replicating adenovirus comprising the REIC C domain DNA (oncolytic Ad-REC domain) according to the present invention administered to a subject of a human or another mammal is delivered to a cancer cell in the subject. The cancer cell is killed via the effect of the oncolytic adenovirus, and full-length REIC protein or REIC C domain protein is expressed in the cancer cell, and selectively induces cancer cell death through endoplasmic reticulum stress in its expression, and simultaneously activates cancer immunity and suppresses the tumor cell growth, and thus the therapeutic effect on cancer is exerted. The anticancer immune activity due to REIC not only acts on a cancer cell locally, but also provides strong, systemic activation of anticancer immunity. The conditionally replicating adenovirus comprising the full length REIC DNA (oncolytic Ad-REIC) and conditionally replicating adenovirus comprising the REIC C domain DNA (oncolytic Ad-REC domain) provide a stronger anticancer effect through a synergistic effect of the cancer-killing effect of the conditionally replicating adenovirus itself and the anticancer effect, for example, due to the anticancer immune activity of REIC. The present invention encompasses virus formulations for cancer treatment comprising such a conditionally replicating adenovirus (oncolytic Ad, oncolytic Ad-REIC, oncolytic Ad-REIC domain). Examples of cancer to be treated include, but are not limited to, brain/nerve tumor, skin cancer, gastric cancer, lung cancer, liver cancer, lymphoma/leukemia, colon cancer, pancreatic cancer, anal/rectal cancer, esophageal cancer, uterine cancer, breast cancer, adrenal cancer, kidney cancer, renal pelvis cancer, bladder cancer, prostate cancer, urethral cancer, penis cancer, testicular cancer, osteosarcoma, leiomyoma, rhabdomyoma, and mesothelioma. The conditionally replicating adenovirus (oncolytic Ad, oncolytic Ad-REIC, oncolytic Ad-REIC domain) according to the present invention may be used for treatment of primary cancer or metastatic cancer.

The conditionally replicating adenovirus (oncolytic Ad, oncolytic Ad-REIC, oncolytic Ad-REIC domain) according to the present invention may be administered by using a method available in the field of gene therapy, and examples thereof include intravascular administration such as intravenous administration and intraarterial administration, oral administration, intraperitoneal administration, intrathoracic administration, intratracheal administration, intrabronchial administration, subcutaneous administration, and transdermal administration.

The conditionally replicating adenovirus (oncolytic Ad, oncolytic Ad-REIC, oncolytic Ad-REIC domain) according to the present invention is suitably administered in a therapeutically effective amount. Those skilled in the art of gene therapy could easily determine the therapeutically effective amount. In addition, the dose may be appropriately changed in accordance with the seriousness of pathological condition, sex, age, body weight, habit, etc., of a subject. A carrier, a diluting agent, and a diluent which are commonly used in the field of drug formulation are comprised. Example of carriers and diluents to be used for a tablet include lactose and magnesium stearate. Example of aqueous solutions to be used for injection include saline and isotonic solutions comprising glucose or other adjuvants, which may be used in combination with a suitable solubilizing agent, for example, an alcohol or a polyalcohol such as propylene glycol, an nonionic surfactant, or the like. Examples of oily solutions to be used include sesame oil and soybean oil, which may be used in combination with a solubilizing agent such as benzyl benzoate and benzyl alcohol.

EXAMPLES

The present invention will be specifically described with reference to the following Examples, but the present invention is never limited to these Examples.

Example 1 Production of Oncolytic Adenoviruses (Oncolytic Adenovirus: Oncolytic Ad)

To produce oncolytic adenoviruses to express REIC or REIC C domain (REIC-C) and decorin (DCN) in the E1 region and E3 region, respectively, a pCA14 Ad E1 shuttle vector to express the REIC or REIC C was first produced. The REIC or REIC C gene was cut out of pShuttole/REIC or REIC-C with NheI-blunt-HindIII, and was subcloned into the pCA14 Ad E1 shuttle vector digested in advance with XbaI-blunt-HindIII. The pCA14/REIC and pCA14/REIC-C vectors were digested with BglII, and then were each cloned into a pΔE1sp1B-HmT-Rd19 shuttle vector (Kim E et al., Hum Gene Ther 2003; 14:1415-1428; Kim J H et al., J Natl Cancer Inst 2006; 98:1482-1493) whose CMV-REIC-polA and AMV-REIC-C-polA expression cassettes had been digested in advance with BglII to obtain pΔE1sp1B-HmT-Rd19/REIC and pΔE1sp1B-HmT-Rd19/REIC-C adenovirus E1 shuttle vectors. A pSP72-E3/DCN (I-K Choi et al., Gene Therapy 2010; 17:190-201.) E3 shuttle vector was linearized with XmnI, with which homologous recombination was conducted via cotransformation of a BJ5183 E. coli strain together with an adenovirus total vector del-RGD linearized with SpeI. As a result, an adenovirus vector del-RGD/DCN with no replication capability was obtained. Newly constructed pΔE1sp1B-HmT-Rd19/REIC and pΔE1sp1B-HmT-Rd19/REIC-C adenovirus E1 shuttle vectors were digested to linearize with XmnI, with which homologous recombination was then conducted via cotransformation of a BJ5183 E. coli strain together with the del-RGD/DCN digested with BstBI. As a result, tumor-specific oncolytic adenoviruses to express REIC or REIC-C and decorin were obtained. The plasmid DNA was digested with PacI, and introduced into a 293A cell for replication.

Purification of an adenovirus, titer measurement, and qualitative analysis were carried out in accordance with the description of Yoo J Y et al., Mol Ther 2007; 15:295-302.

The oncolytic adenovirus vector comprising no REIC is referred to as oncolytic Ad, the oncolytic adenovirus vector comprising the full length REIC DNA is referred to as oncolytic Ad-REIC, and the oncolytic adenovirus vector comprising the REIC C domain DNA is referred to as oncolytic Ad-REIC domain.

Example 2 Expression of REIC Protein in Various Cells by Addition of Oncolytic Ad, Oncolytic Ad-REIC, and Oncolytic Ad-REIC Domain Method To measure expression of REIC protein after treatment with the Ad-REIC, cells were seeded in a flat-bottomed 6-well plate and incubated for 24 hours. The cells were infected with an adenovirus at an MOI (multiplicity of infection) as set forth in Figures in a complete medium (300 μL) for 1 hour, and washed with PBS (phosphate buffered saline) twice, and lysed with a lysis buffer (50 mM HEPES, pH 7.4, 250 mM NaCl, 1 mM EDTA, 1% NP-40, 1 mM DTT, 1 mM PMSF, 5 μg/mL leupeptin, 5 μg/mL aprotinin, 2 mM $Na_3VO_4$, 1 mM NaF, 10 mM β-GP) to extract REIC protein.

After centrifugation, the supernatant was diluted with an identical volume of 4×SDS sample buffer, and heated at 95° C. for 5 minutes. A sample (protein: 5 μg) was separated on a 10% SDS-PAGE gel, and electrophoretically transferred onto a polyvinylidene fluoride (PVDF) membrane. The blot transferred was blocked with a 5% skim milk powder and 0.1% Tween-20-containing TBS (Tris-buffered saline) at room temperature for 1 hour. The resultant was then reacted with a mouse monoclonal anti-human REIC/Dkk-3 antibody (1:1000 dilution) (primary antibody) and thoroughly washed with 0.1% Tween-20-containing TBS (T-TBS), and thereafter reacted with a secondary antibody labeled with horseradish peroxidase. After further washing with T-TBS, the resultant was allowed to develop color by using an ECL kit (Amersham Pharmacia Biotech Inc., Chandler, Ariz.), a kit for chemiluminescence detection. The band for REIC protein is found around 60 kDa in western blotting.

Results

Figure 3:
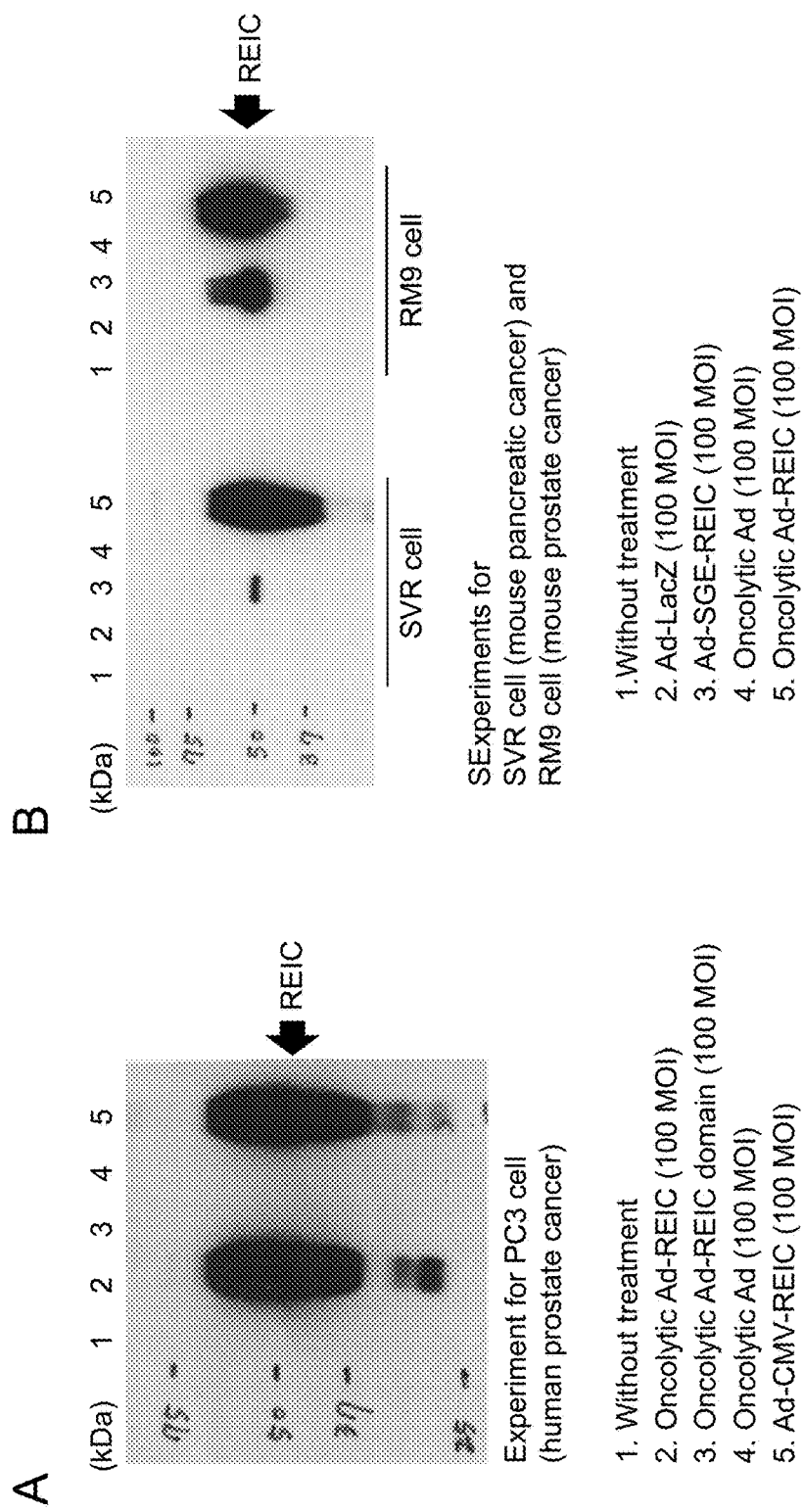
FIG. 3 shows expression of REIC protein in various cells by addition of an oncolytic adenovirus.

FIG. 3 shows expression of REIC protein in various cells by addition of the oncolytic Ad (adenovirus), oncolytic Ad-REIC, and oncolytic Ad-REIC domain in western blot analysis.

In each cell, addition of the oncolytic Ad-REIC allows for expression of REIC protein at a level comparable to or higher than conventional Ad-REICs. REIC protein is known to have an effect of activating anticancer immunity in vivo (WO2009/119874), and thus the oncolytic Ad-REIC is also expected to have an effect of activating anticancer immunity in vivo.

Figure 4:
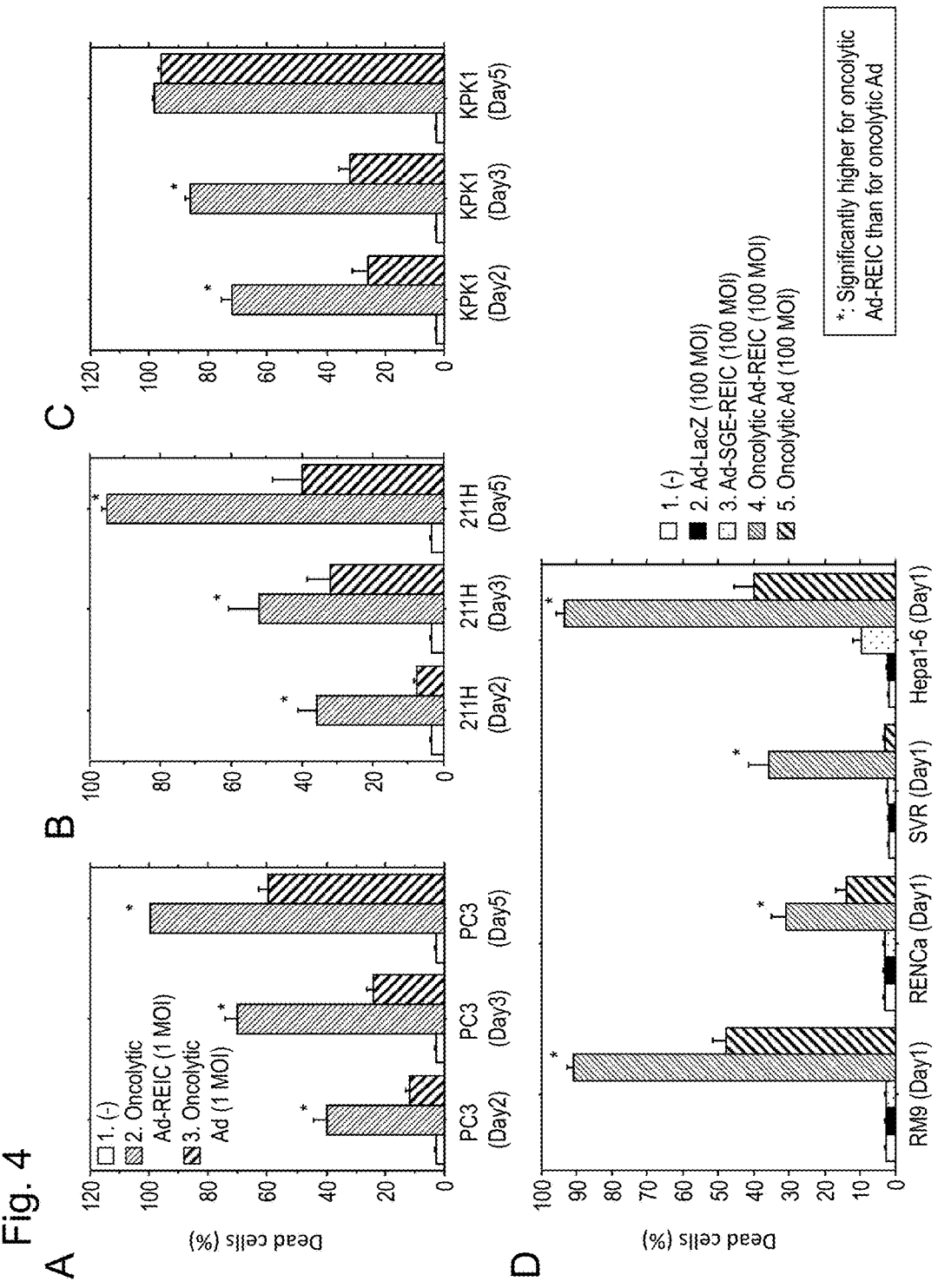
FIG. 4 shows graphs of cell death-inducing rates in various cells by addition of oncolytic adenoviruses (oncolytic Ad and oncolytic Ad-REIC).
Figure 5:
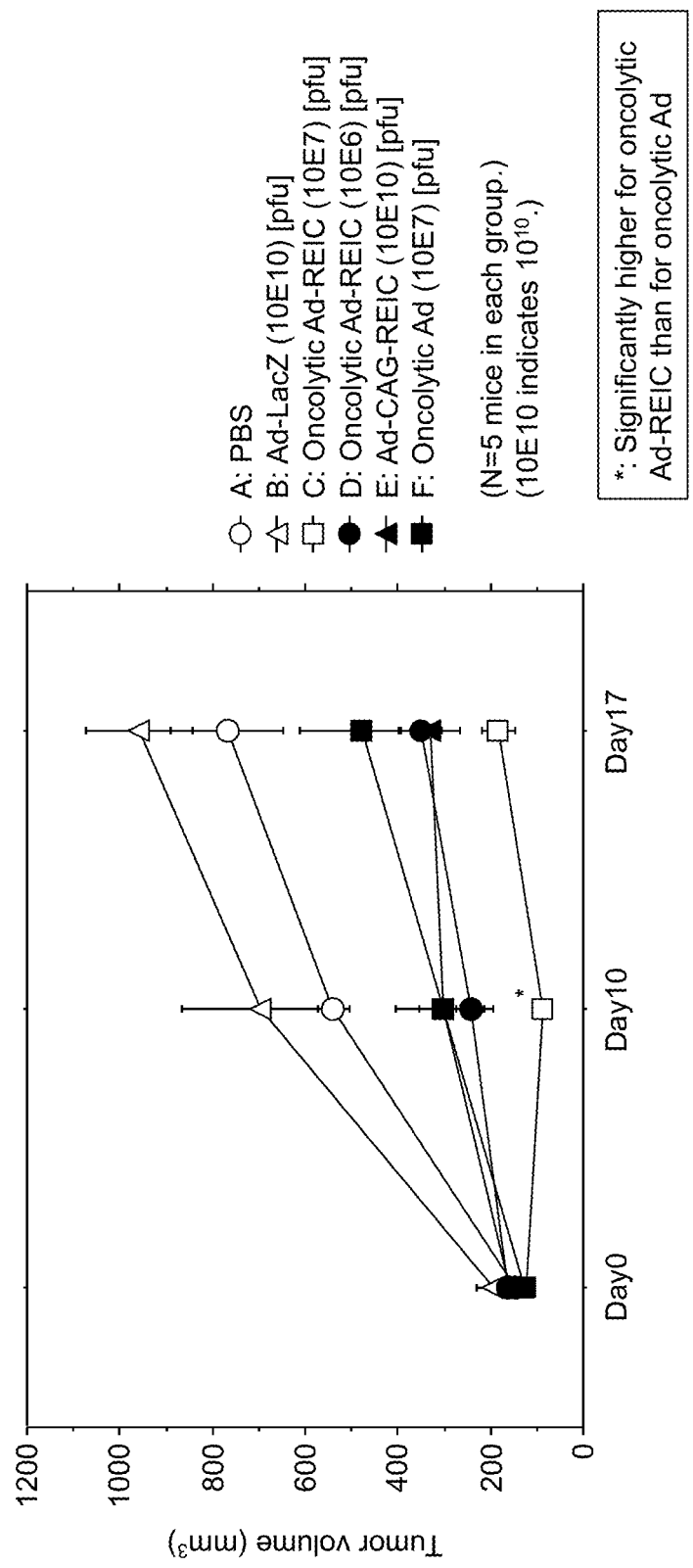
FIG. 5 is a graph of the change of tumor volume in mice administered with oncolytic adenoviruses (oncolytic Ad and oncolytic Ad-REIC).
Figure 6:
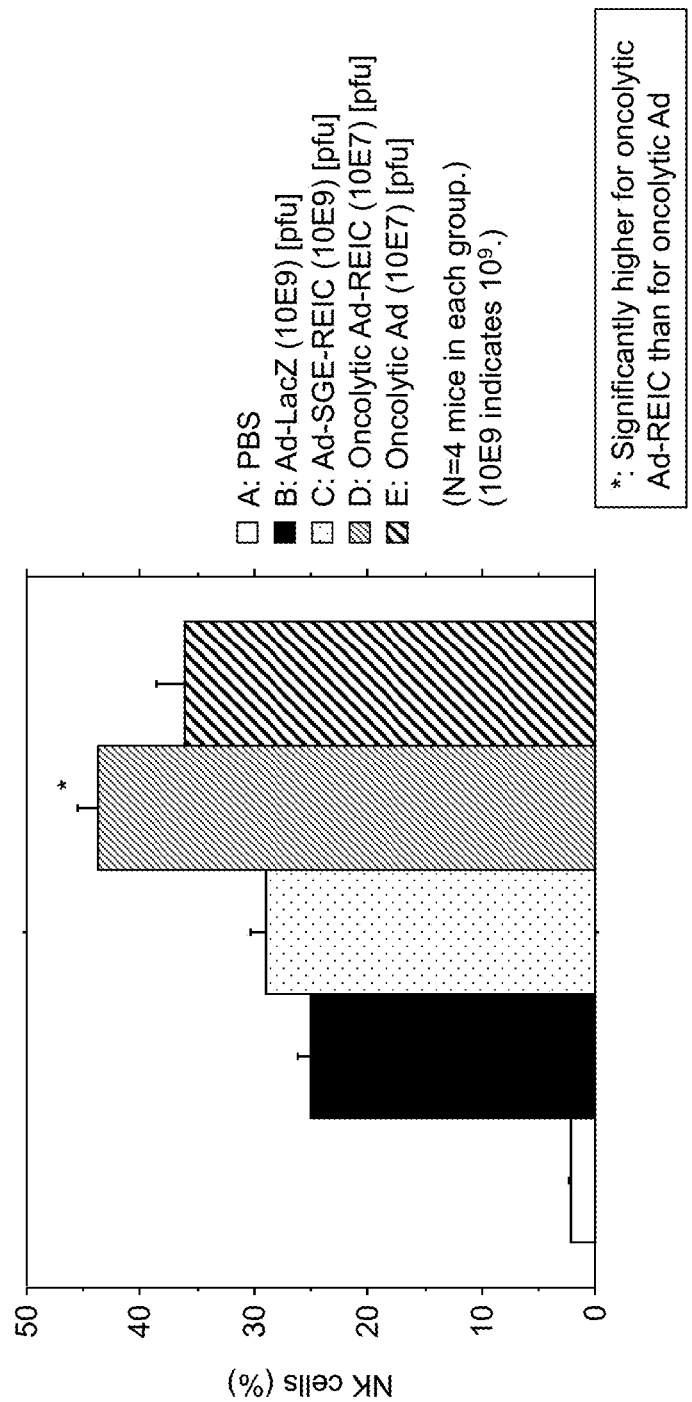
FIG. 6 is a graph of NK cell induction in mice administered with oncolytic adenoviruses (oncolytic Ad and oncolytic Ad-REIC).

Example 3 Investigation of Cell Death-Inducing Rate in Various Cells by Addition of Oncolytic Ad and Oncolytic Ad-REIC Method To investigate the cell-killing rate after treatment with the Ad-REIC, cells were seeded in a flat-bottomed 6-well plate and incubated for 24 hours. The cells were treated with an adenovirus at an MOI (multiplicity of infection) as set forth in Figures in a complete medium (300 µL) for 1 hour, and 1700 µL of a fresh medium was added thereto. On the days as set forth in Figures, the dead cell ratio (%) was measured in microscopic observation for 5 views. In FIGS. 4 to 6, data are represented as average±standard deviation. For the statistical significance test, analysis of variance or a Mann-Whitney U test was performed. $p<0.05$ was determined to have a significant difference.

Results

FIG. 4 shows the cell death-inducing rate in various cells by addition of the oncolytic Ad and oncolytic Ad-REIC. As shown in FIG. 4, the oncolytic Ad-REIC induced cell death at a significantly higher level than other compounds.

Example 4 Therapeutic Effect of Oncolytic Ad and Oncolytic Ad-REIC on Human Prostate Cancer Method To the right femur of an adult male nude mouse, $2 \times 10^6$ cells/0.1 mL PBS of PC3 human prostate cancer cells was administered via subcutaneous injection. After 10 days, when the tumor volume reached 200 to 300 $mm^3$, an adenovirus was intratumorally administered (Day 0 in FIG. 5). The tumor volume was calculated by using the formula ½ (w1×w2×w2). In this formula, w1 and w2 denote the maximum tumor diameter and the minimum tumor diameter, respectively.

Results

FIG. 5 shows the results. As shown in FIG. 5, a dose-dependent therapeutic effect was found in the case that the oncolytic Ad-REIC was used. The oncolytic Ad-REIC had a higher effect ($10^7$) than other treatment groups. No clear toxicity was found for all of the mice subjected to the experiment.

Example 5 NK Cell-Inducing Effect of Oncolytic Ad and Oncolytic Ad-REIC

Method

To the left and right femurs of an adult male nude mouse, $2 \times 10^6$ cells/0.1 mL PBS of PC3 human prostate cancer cells was administered via subcutaneous injection. This mouse was a mouse tumor model having at least two tumor sites. After 10 days, when the tumor volume in both sides reached 200 to 300 $mm^3$, an adenovirus was administered into the right tumor. Three days after the vector injection, natural killer (NK) cells in the peripheral lymphocytes were counted by using flow cytometry with an anti-NK cell antibody (eBioscience Inc., 10255 Science Center Drive, San Diego, Calif. 92121, USA).

Results

FIG. 6 shows the results. As shown in FIG. 6, the NK cell-inducing effect in the case that the oncolytic Ad-REIC was used was significantly higher than those of other treatment groups.

Example 6 Induction of Antigen-Specific Immune Response by Oncolytic Ad and Oncolytic Ad-REIC Method A cancer model was produced with an immune-competent mouse, and study was conducted for identification of a cancer-specific CTL cell, which serves for anticancer immunity, after intratumoral administration of the oncolytic Ad-REIC or oncolytic Ad. A malignant thymoma cell [EG-7] strain ($1.0 \times 10^6$ cells) into which an OVA (ovalbumin) gene as a foreign antigen had been introduced was subcutaneously transplanted to a C57/BL6 mouse having a normal immune system to produce a cancer mouse model. When the tumor diameter reached 100 $mm^3$ or larger, the oncolytic Ad-REIC or oncolytic Ad was injected into the tumor (dose: $1.0 \times 10^6$ pfu/tumor). Three days after the treatment, the tumor was collected and the fraction of CTLs positive for OVA-specific CD8 in the tumor-infiltrating lymphocytes (TIL) was dynamically analyzed by using flow cytometry with a CD8 antibody and an OVA tetramer (antibody which recognizes H-2kb-restricted OVA epitope).

Results

Figure 7:
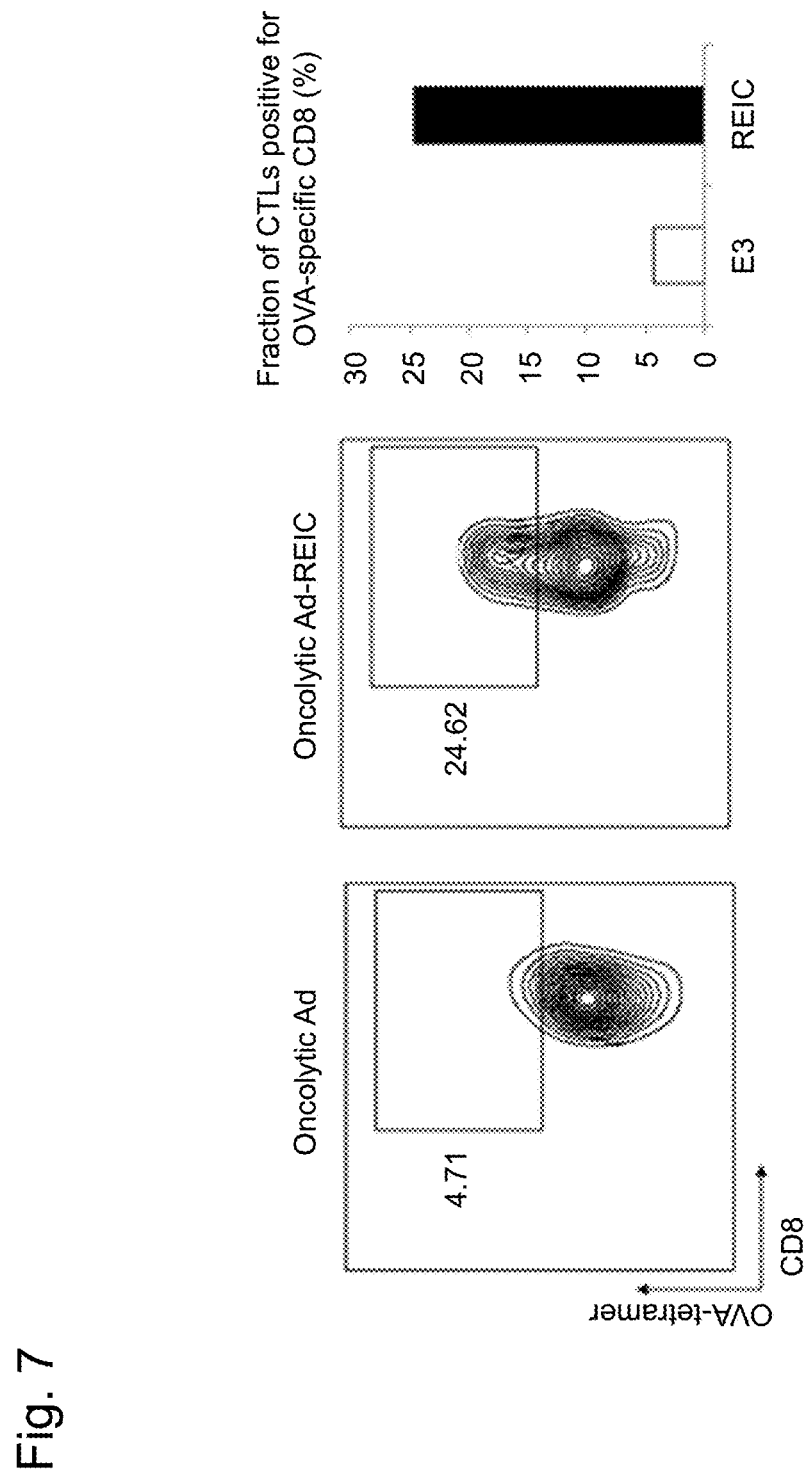
FIG. 7 shows induction of antigen-specific immune response in the case that oncolytic adenoviruses (oncolytic Ad and oncolytic Ad-REIC) were administered as results of analysis for tumor-infiltrating lymphocytes (TIL).

FIG. 7 shows the results. As shown in FIG. 7, the frequency of tetramer-positive CD8 cells was larger in the tumor in the mouse administered with the oncolytic Ad-REIC. In other words, administration of the oncolytic Ad-REIC induced a higher OVA antigen-specific immune response than administration of the oncolytic Ad. In view of the results of this experiment, administration of the oncolytic Ad-REIC, which encodes the REIC gene and expresses REIC protein, is expected to allow for induction of cancer-specific immune response.

INDUSTRIAL APPLICABILITY

The conditionally replicating adenovirus according to the present invention can be used for treatment of cancer.

SEQUENCE LISTING FREE TEXT

SEQ ID NO: 1, 2, 3, 8, 9, 10 synthetic

All of the publications, patents, and patent applications cited herein are wholly incorporated herein by reference.

The invention claimed is:

1. A conditionally replicating adenovirus that replicates specifically in a cancer cell and expresses REIC protein or REIC C domain protein, comprising:
   (a) a DNA sequence encoding a REIC protein selected from the group consisting of a full-length REIC protein and a REIC C domain protein;
   (b) an ITR (inverted terminal repeat) sequence of an adenovirus type 5 genome; an insertion of at least one HRE sequence, an hTERT promoter, a decorin-encoding DNA, and a DNA encoding a peptide comprising an RGD sequence, wherein
      (i) the hTERT promoter is an hTERT promoter modified through addition of a c-Myc binding site and an Sp1 binding site;
      (ii) six HRE sequences each consisting of a nucleotide sequence as set forth in SEQ ID NO: 3 are inserted upstream of the hTERT promoter;
      (iii) an Rb binding region (Retinoblastoma gene binding region), being a part of an E1A region, in the adenovirus type 5 genome sequence as set forth in as SEQ ID NO: 4 is deleted;
      (iv) nucleotides of a portion encoding E1B-19 kDa, being a part of an E1B region, in the adenovirus type 5 genome sequence as set forth in as SEQ ID NO: 4 are deleted;
      (v) an E3 region is partially deleted;
      (vi) a DNA construct consisting of a promoter sequence, the decorin-encoding DNA, and a poly A addition sequence is inserted into the E3 region;
      (vii) the DNA encoding a peptide comprising an RGD sequence is inserted into the E3 region; and
      (viii) a DNA construct consisting of a CMV promoter sequence, a DNA encoding REIC DNA or REIC C domain DNA, and a poly A addition sequence is inserted into an E1 region.

2. The conditionally replicating adenovirus according to claim 1, wherein
   (ix) 24 nucleotides at positions 923 to 946 as the Rb binding region (Retinoblastoma gene binding region), being a part of the E1A region, in the adenovirus type 5 genome sequence as set forth in SEQ ID NO: 4 are deleted;
   (x) nucleotides at positions 1722 to 1986 as the portion encoding E1B-19 kDa, being a part of the E1B region, in the adenovirus type 5 genome sequence as set forth in as SEQ ID NO: 4 are deleted; and
   (xi) nucleotides at positions 28592 to 30479, being a part of the E3 region, in the adenovirus type 5 genome sequence as set forth in as SEQ ID NO: 4 are deleted.

3. The conditionally replicating adenovirus according to claim 1, wherein the REIC protein is a full length REIC protein.

4. The conditionally replicating adenovirus according to claim 1, wherein the REIC protein is a REIC C domain protein.

5. A cancer therapeutic agent comprising the conditionally replicating adenovirus according to claim 1 as an active ingredient.

6. The cancer therapeutic agent according to claim 5, wherein the conditionally replicating adenovirus replicates specifically in a cancer cell and expresses REIC protein, and wherein the expressed REIC protein induces cancer cell death through endoplasmic reticulum stress and induces a systemic anticancer immune activity.

* * * * *